(12) United States Patent
Carpenter et al.

(10) Patent No.: US 11,918,497 B2
(45) Date of Patent: Mar. 5, 2024

(54) STENT AND METHOD OF MAKING SAME

(71) Applicant: Vactronix Scientific LLC, Fremont, CA (US)

(72) Inventors: Scott P. Carpenter, Fremont, CA (US); Julio C. Palmaz, Napa, CA (US)

(73) Assignee: Vactronix Scientific, LLC, San Antonio, TX (US)

( * ) Notice: Subject to any disclaimer, the term of this patent is extended or adjusted under 35 U.S.C. 154(b) by 195 days.

(21) Appl. No.: 17/372,990

(22) Filed: Jul. 12, 2021

(65) Prior Publication Data

US 2022/0031483 A1 Feb. 3, 2022

Related U.S. Application Data

(62) Division of application No. 16/287,519, filed on Feb. 27, 2019, now Pat. No. 11,058,564.

(51) Int. Cl.
*A61F 2/82* (2013.01)
*A61F 2/915* (2013.01)

(52) U.S. Cl.
CPC .... *A61F 2/915* (2013.01); *A61F 2002/91533* (2013.01); *A61F 2002/91541* (2013.01); *A61F 2002/91558* (2013.01); *A61F 2002/91566* (2013.01); *A61F 2210/0014* (2013.01); *A61F 2230/0054* (2013.01); *A61F 2240/001* (2013.01); *A61F 2250/0067* (2013.01); *A61F 2250/0068* (2013.01); *A61F 2250/0098* (2013.01); *A61L 2420/02* (2013.01)

(58) Field of Classification Search
CPC .............................. A61F 2/82; A61F 2230/00
USPC ...................... 623/1.13, 1.15; 427/2.24, 2.25
See application file for complete search history.

(56) References Cited

U.S. PATENT DOCUMENTS

| | | | |
|---|---|---|---|
| 6,231,598 B1 | 5/2001 | Berry et al. | |
| 6,805,898 B1 * | 10/2004 | Wu | A61F 2/0077 216/10 |
| 7,744,644 B2 | 6/2010 | Weber et al. | |
| D665,079 S | 8/2012 | Zago | |
| D665,080 S | 8/2012 | Zago | |

(Continued)

FOREIGN PATENT DOCUMENTS

| | | |
|---|---|---|
| WO | 199725937 A1 | 7/1997 |
| WO | 2007117645 A2 | 10/2007 |

OTHER PUBLICATIONS

Feiring, AJ, "Below-the-Knee Drug-Eluting Stents," Endovascular Today, pp. 65-72 (Aug. 2011).

(Continued)

*Primary Examiner* — Cachet I Proctor
(74) *Attorney, Agent, or Firm* — Rosenbaum IP, P.C.; David G. Rosenbaum

(57) ABSTRACT

A stent for vascular interventions having a hybrid open cell geometry. Variants of the stent include bare metal stents and drug-eluting stents. Embodiments of the stent include end projections for radiopaque markers or a discontinuous partial radiopaque coating on low-stress or low-strain regions of the peripheral stent. The stents of the invention are characterized by having thin walls, nested rows of struts, high expansion ratio, high and uniform radial force over entire diametric size and length of device, crush resistance up to and including about 90% of its fully expanded diameter, high fatigue resistance and high corrosion resistance.

26 Claims, 17 Drawing Sheets

(56) References Cited

U.S. PATENT DOCUMENTS

| | | | |
|---|---|---|---|
| 8,353,949 B2 | 1/2013 | Weber et al. | |
| D723,165 S | 2/2015 | Chanduszko | |
| D723,166 S | 2/2015 | Igaki et al. | |
| 8,998,971 B1 * | 4/2015 | Kelly | A61F 2/07 623/1.11 |
| 9,138,512 B2 | 9/2015 | Ferrari et al. | |
| D740,427 S | 10/2015 | McDonnell et al. | |
| 9,320,929 B2 | 4/2016 | Cottone, Jr. et al. | |
| 2003/0055485 A1 * | 3/2003 | Lee | A61F 2/91 623/1.15 |
| 2004/0225347 A1 | 11/2004 | Lang | |
| 2004/0243097 A1 | 12/2004 | Falotico et al. | |
| 2005/0180919 A1 * | 8/2005 | Tedeschi | A61L 31/18 424/9.4 |
| 2005/0228477 A1 | 10/2005 | Grainger et al. | |
| 2006/0111771 A1 * | 5/2006 | Ton | A61F 2/962 623/1.15 |
| 2007/0021828 A1 * | 1/2007 | Krolik | A61F 2/958 623/1.31 |
| 2008/0051875 A1 * | 2/2008 | Cottone | A61F 2/844 623/1.49 |
| 2008/0132995 A1 * | 6/2008 | Burgermeister | A61L 31/18 623/1.42 |
| 2008/0221666 A1 * | 9/2008 | Licata | A61F 2/95 623/1.22 |
| 2008/0294231 A1 * | 11/2008 | Aguilar | A61F 2/95 623/1.11 |
| 2010/0004733 A1 * | 1/2010 | Atanasoska | A61F 2/86 623/1.15 |
| 2010/0305682 A1 | 12/2010 | Furst | |
| 2011/0106239 A1 | 5/2011 | Goto | |
| 2011/0160839 A1 * | 6/2011 | Weber | A61F 2/91 623/1.42 |
| 2011/0190871 A1 * | 8/2011 | Trollsas | A61F 2/82 623/1.15 |
| 2011/0196475 A1 * | 8/2011 | Kitaoka | A61F 2/966 623/1.11 |
| 2011/0245904 A1 * | 10/2011 | Pacetti | A61F 2/915 623/1.42 |
| 2013/0261723 A1 * | 10/2013 | Stankus | A61M 25/104 623/1.42 |
| 2014/0277391 A1 | 8/2014 | Layman et al. | |
| 2015/0238334 A1 * | 8/2015 | Kang | A61F 2/915 623/1.15 |
| 2015/0374521 A1 * | 12/2015 | Zheng | A61F 2/915 623/1.2 |

OTHER PUBLICATIONS

U.S. Department of Health and Human Services Food and Drug Administration, "Non-Clinical Engineering Tests and Recommended Labeling for Intravascular Stents and Associated Delivery Systems," Guidance for Industry and FDA Staff, pp. 1-55 (Apr. 18, 2010).

U.S. Department of Health and Human Services Food and Drug Administration, "Select Updates for Non-Clinical Engineering Tests and Recommended Labeling for Intravascular Stents and Associated Delivery Systems," Guidance for Industry and Food and Drug Administration Staff, pp. 1-10 (Aug. 15, 2015).

PCT Written Opinion of the International Searching Authority, International Application No. PCT/US2020/019984 (dated Jul. 6, 2020).

PCT Notification of Transmittal of the International Search Report and the Written Opinion of the International Searching Authority, or the Declaration. International Application No. PCT/US2020/19984. (dated Jul. 6, 2020).

* cited by examiner

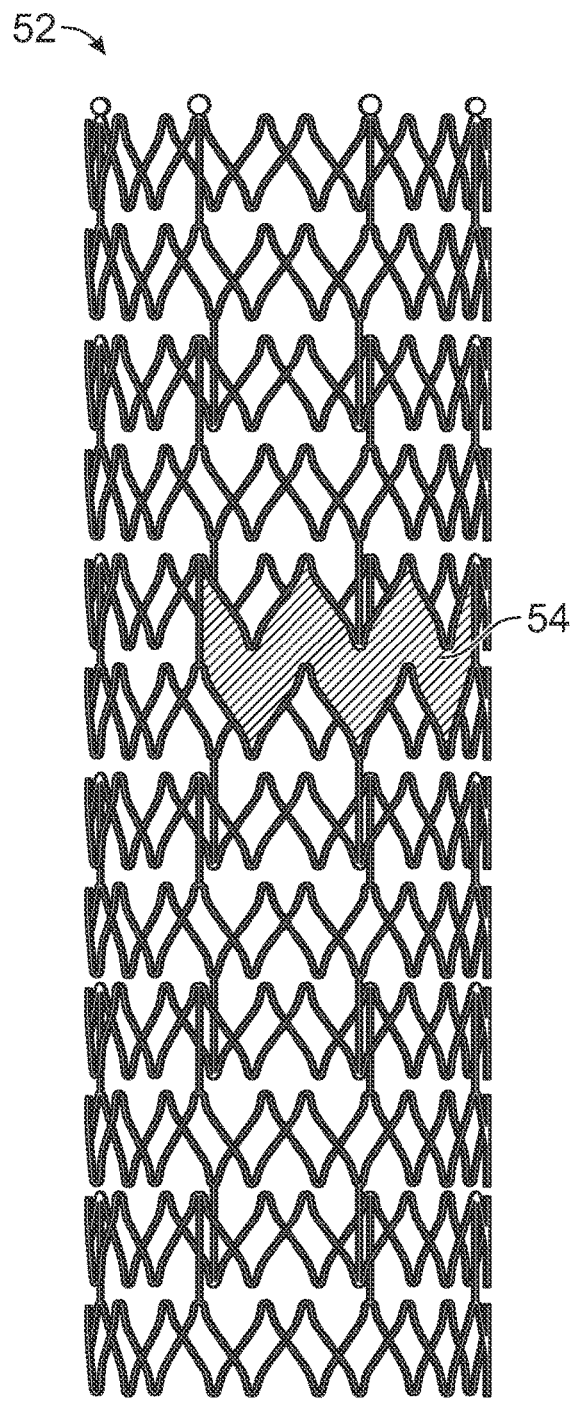
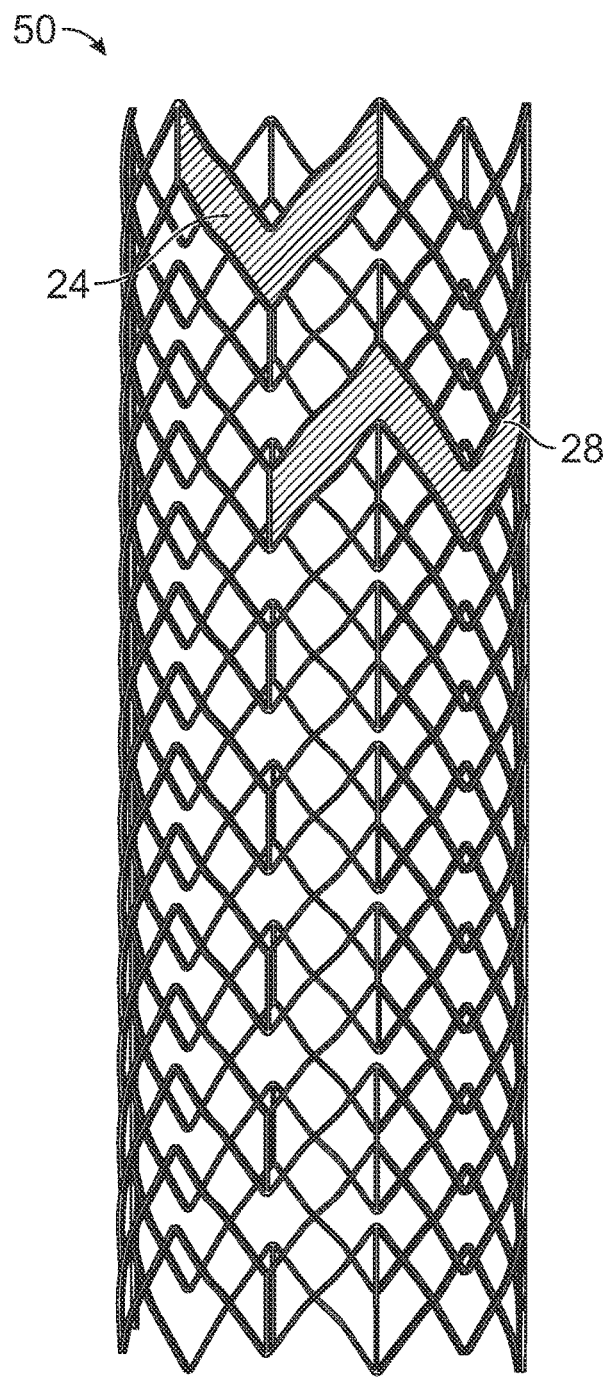
FIG. 5
(Prior Art)
FIG. 6

STENT AND METHOD OF MAKING SAME

CROSS REFERENCE TO RELATED APPLICATIONS

This is a divisional application of commonly assigned U.S. patent application Ser. No. 16/287,519 filed Feb. 27, 2019, now U.S. Pat. No. 11,058,564, which is hereby incorporated by reference in its entirety.

BACKGROUND OF THE INVENTION

The present invention pertains generally to endoluminal stents used in minimally invasive procedures to restore and maintain patency of anatomic passageways. More particularly, the present invention relates to vascular stents capable of percutaneous delivery to blood vessels, including coronary, neurovascular and peripheral vessels requiring restoration of blood flow and maintenance of vascular patency. Still more particular, the present invention pertains to a below-the-knee intravascular stent characterized by having thin walls, nested circumferential rows of struts, high expansion ratio, high and uniform radial force over entire diametric size and length of device, crush resistance to at least 90% of its fully expanded diameter, high fatigue resistance and high corrosion resistance.

Stenting of peripheral blood vessels, particularly below-the-knee stenting, presents challenges that are not met by the current use of coronary stent designs applied in a peripheral intervention. Due to particularly difficult device design and delivery requirements of below-the-knee stenting, percutaneous transluminal angioplasty (PTA) also known as balloon angioplasty of the anterior or posterior tibial arteries or the peroneal artery is the current standard intervention protocol for ischemic artery disease in this anatomical region. There is, however, substantial agreement that stand-alone balloon angioplasty of the below the knee arteries is sub-optimal because lesions in this region tend to be highly complex with risk factors including small arterial diameter, lesion length, vascular dissections, diabetes and/or poor arterial run off. It has been observed that after one year post-PTA freedom from amputation, restenosis, or reintervention was only 18%. Feiring, A. J., "Below-the-Knee Drug-Eluting Stents," *Endovas. Today, August* 2011, pp. 65-72. Feiring reviewed data supporting the overall efficacy of bare metal stents (BMS) and drug-eluting stents (DES) in treating below-the-knee chronic limb ischemia (CLI) and found that the below-the-knee DES registry data report 1,854 DES implanted in 765 limbs with CLI. There are an additional 517 patients who have been randomized to balloon angioplasty or BMS versus DES. With the exception of a single paclitaxel DES study, all of the reported studies are concurrent in their findings, reporting that DES for CLI is a safe and effective treatment that is superior to either balloon angioplasty or BMS.

Particular study findings included the ACHILLES trial which randomized CLI patients to either the CYPHER DES (Cordis Corporation, Bridgewater, NJ) or percutaneous transluminal angioplasty (PTA). The binary restenosis rates after 1 year were 19% with the CYPHER DES and 49% with angioplasty. The DESTINY trial randomized patients to the XIENCE DES (Abbott Vascular, Santa Clara, CA) versus the MULTILINK VISION BMS (Abbott Vascular). Primary patency rates at 1 year were 85% versus 54%, and target lesion revascularization was 9% versus 34% with DES versus BMS, respectively. The YUKON-BTK trial compared a proprietary non-polymer sirolimus stent to the same uncoated BMS. The 1-year primary patency rate for DES was 81% versus 56% for the BMS. Thus, after 1 year, all three randomized trials strongly endorsed the superiority of DES over balloon PTA or BMS.

While the data suggests that drug-eluting stenting of below-the-knee lesions is desirable, to date the commercially available drug-eluting stents have not achieved commercial success in the marketplace. The CYPHER DES (Cordis Corporation) was discontinued in 2011 due to poor sales. The XIENCE PRIME DES (Abbott Vascular) is a coronary stent that was not approved by the U.S. Food and Drug Administration (USFDA) for below-the-knee indications. Similarly, the MULTI-LINK VISION BMS is a coronary stent which also has not been approved by the USFDA for below-the-knee indications.

Additionally, the ZILVER PTX DES (Cook Medical, Bloomington, IN) is a coronary stent design that has been approved by the USFDA for above-the-knee femoropopliteal artery disease. Finally, the STENTYS BTK (Stentys, Paris, France) DES stent has been used in below-the-knee interventions and is the first BTK DES approved by the Notified Body for commercial sale in Europe. The STENTYS BTK has not been approved by the USFDA for below-the-knee interventions.

Each of these prior devices have been coronary stent designs that have been employed in peripheral, particularly, below-the-knee vascular interventions. Heretofore, however, it has been unknown to design bare metal and/or drug-eluting stents to have properties that are optimally designed for delivery to and deployment within the below-the-knee vasculature.

SUMMARY OF THE INVENTION

It is an objective of the present invention to provide a stent configured for delivery to and deployment within the peripheral, particularly below-the-knee, vasculature.

It is a further objective of the present invention to provide a bare metal stent configured for delivery to and deployment within the peripheral, particularly below-the-knee, vasculature.

It is another objective of the present invention to provide a drug-eluting stent configured for delivery to and deployment within the peripheral, particularly below-the-knee, vasculature.

It is yet another objective of the present invention to provide either a bare metal stent or a drug-eluting stent for below-the-knee vascular interventions which is characterized by having a high expansion ratio of up to about 6.4:1.

It is a further objective of the present invention to provide a stent configured for peripheral below-the-knee vascular interventions in which the stent has a crimped delivery diameter down to about 0.84 mm for low crossing profile delivery and is compatible with a 3.5 French delivery system suitable for pedal access.

It is still another objective of the present invention to provide either a bare metal stent or a drug-eluting stent for below-the knee vascular interventions which is characterized by having a wall thickness between about 50 to 100 μm.

It is yet still another objective of the present invention to provide either a bare metal stent or a drug-eluting stent for below-the knee vascular interventions which is characterized by having a uniform radial strength of at least 0.45 N/mm along its entire circumference and length.

It is a further objective of the present invention to provide either a bare metal stent or a drug-eluting stent for below-the knee vascular interventions which is characterized by having a crush resistance to up to about 90% of the expanded diameter of the stent.

It is yet a further objective of the present invention to provide either a bare metal stent or a drug-eluting stent for below-the knee vascular interventions which is characterized by having at least 200% fatigue resistance, as determined by allowable alternating strain, when compared to stents fabricated from wrought materials.

It is still yet a further objective of the present invention to provide either a bare metal stent or a drug-eluting stent for below-the knee vascular interventions which is characterized by having lengths up to and including 200 mm.

It is another objective of the present invention to provide a stent for below-the knee vascular interventions which is characterized by having a micro-textured outer surface configured for drug-loading.

It is still another objective of the present invention to provide a below-the-knee vascular stent having volume-enhancing features in or on the outer surface of the stent and a drug eluting coating on the outer surface and within the volume-enhancing features.

It is a further objective of the present invention to provide a peripheral vascular stent in which the volume-enhancing features in or on the outer surface of the stent increases the surface volume of the stent relative to a stent of like dimensions that does not have the volume-enhancing features.

It is yet another objective of the present invention to provide a below-the-knee vascular stent having volume-enhancing features in or on the outer surface having a depth between about 0.5 µm to about 25 µm, such as between 0.5 µm to about 10 µm, and a spacing between adjacent volume-enhancing features of about 2 µm to about 25 µm.

It is still a further objective of the present invention to provide a below-the-knee vascular stent having a varied thickness profile of a drug-eluting coating that regulates the drug-elution profile when the stent is implanted into a blood vessel.

It is still another objective of the present invention to provide a below-the-knee vascular stent having a plurality of circumferential ring structures interconnected by a plurality of bridge members defining a plurality of open cells.

It is another further objective of the present invention to provide a below-the-knee vascular stent having a first set of open cells at proximal and distal ends of the stent and a second set of open cells, having a different geometry than the first set of open cells, along an intermediate section of the stent between the proximal and distal ends of the stent.

It is yet another objective of the present invention to provide a below-the-knee vascular stent having a layer of radiopaque material on at least a portion of the outer surface of the stent.

It is still another objective of the present invention to provide a below-the-knee vascular stent in which a layer of radiopaque material is selectively provided on low-stress portions of the stent.

It is still yet another objective of the present invention to provide a below-the-knee vascular stent having a plurality of projections extending from opposing proximal and distal ends of the stent, each of the plurality of projections being configured to couple to a radiopaque marker.

It is a further objective of the present invention to provide a below-the-knee vascular stent having a plurality of projections configured as open frame members each having outer structural members defining a central open region bounded by the outer structural members and a radiopaque cuff coupled to the open frame members and substantially occupying the central open region of the projections.

These and other objects, features and advantages of the present invention will be more apparent to those skilled in the art from the following more detailed description of the present invention taken with reference to the accompanying drawings. The above summary is not intended to describe each disclosed embodiment or every implementation of the present invention. The Figures and Detailed Description that follow more particularly exemplify these embodiments.

BRIEF DESCRIPTION OF THE DRAWINGS

FIG. 5 is a side elevational view of a portion of a prior art coronary stent employed in peripheral below-the-knee interventions.

FIG. 6 is a side elevational view of a portion of the inventive stent in accordance with the second embodiment of the present invention.

DETAILED DESCRIPTION OF THE INVENTION

Figure 1:
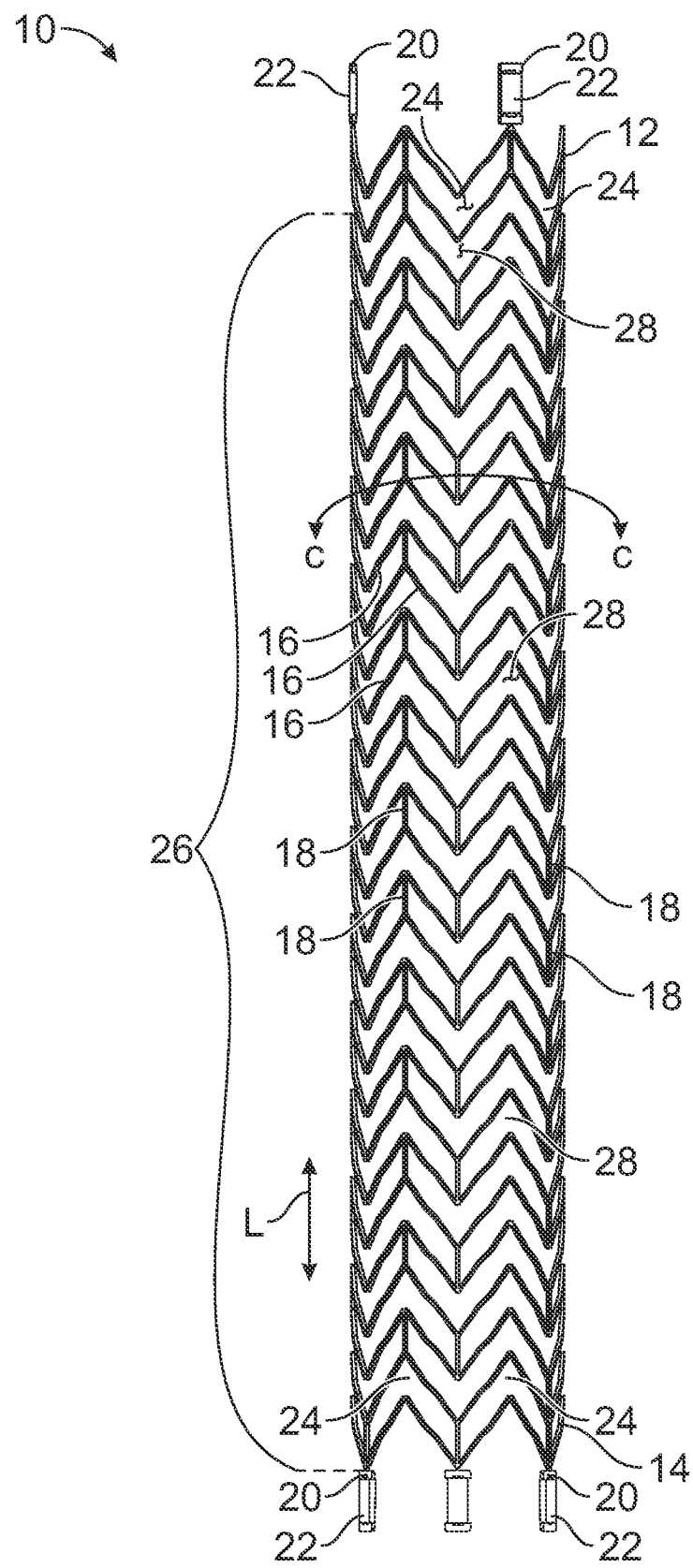
FIG. 1 is side elevational view of a stent in accordance with a first embodiment of the present invention.

The device, system and methods of the present invention will be described with reference to certain exemplary embodiments thereof. These exemplary embodiments are intended to be illustrative and non-limiting examples of the present invention. The example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. Those of ordinary skill in the art will understand and appreciate that variations in materials, structure, material properties, and tolerances may be made without departing from the scope of the invention, which is defined only by the claims appended hereto and their range of equivalents. In some example embodiments, well-known processes, well-known device structures, and well-known technologies are not described in detail.

For ease of understanding, the present invention is described with reference to the accompanying Figures. In the accompanying Figures like elements are identified by like reference numerals.

For purposes of clarity, the following terms used in this patent application will have the following meanings:

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

"Substantially" is intended to mean a quantity, property, or value that is present to a great or significant extent and less than totally.

"About" is intended to mean a quantity, property, or value that is present at ±10%. Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

"Shape memory alloy" is intended to mean a binary, ternary, quaternary metal alloy that recover apparent permanent strains when raised above an Austenitic transformation temperature ($A_s$). Shape memory alloys have two stable phases, i.e., a high-temperature or Austenite phase and a low-temperature or Martensite phase.

"Superelastic" is intended to mean a property of a material characterized by having a reversible elastic response in response to an applied stress. Superelastic materials exhibit a phase transformation between the austenitic and martensitic phases as the applied stress is loaded or unloaded.

"Radiopaque" is intended to mean any material that obstructs passage of radiation and increases contrast to X-ray or similar radiation imaging.

"Sinusoidal" is intended to mean a structure having a wave-form pattern characterized by sine and cosine functions as well as a wave-form pattern that is not rigorously characterized by those functions but nevertheless resemble such in a more general way. As a general example, a waveform pattern includes those characterized as having one or more peaks and valleys that are generally U-shaped, bulbous, or are more triangular in shape, such as V-shaped, zig-zag, or saw-tooth shaped, or whose peaks and valleys are generally square or rectangular.

The terms "peak" and "valley" shall be defined with respect to the proximal and distal opposing ends of the stent. Moreover, for the sake of clarity, the terms "peak" and "valley" in reference to circumferential ring member or sub-element thereof are intended to include not only the point(s) of maximum or minimum amplitude on a circumferential ring, but also a small region around the maximum or minimum. More precisely, in the case of peaks, the 'small region' around the maximum is intended to include any point along the ring member which is distal of a line extending through the innermost part of the ring member at the maximum amplitude and perpendicular to the longitudinal axis of the stent up to the peak itself. In the case of valleys, the 'small region' around the minimum is intended to include any point along the ring member which is proximal of a line extending through the innermost part of the ring member at the minimum amplitude and perpendicular to the longitudinal axis of the stent up to the valley itself.

The term "volume-enhancing feature" is intended to mean a topographical feature on or in an abluminal (outer) or luminal (inner) surface of a stent that increases the surface area or surface volume of the stent when compared to a stent surface without the volume-enhancing feature. Examples of such topographical volume-enhancing features include, without limitation, surface depressions such as grooves or trenches and surface protrusions such as pyramidal, conical, columnar, cylindrical, cubic or other polygonal projections. Surface volume may be determined by conventional measurement methods, such as, for example, ISO 4287:1997 or ASTM D4417. For purposes of this application, the term "groove" or "grooves" is used for ease of reference and illustration and as an example of a volume-enhancing feature. The terms "groove" and "volume-enhancing feature" are used interchangeably in this description.

Several alternative variants of the present invention are illustrated in the accompanying Figures. The embodiments of the peripheral below-the-knee stent are characterized by a tubular stent having a plurality of generally sinusoidal circumferential ring members with adjacent ring members being interconnected by at least one bridge member extending between a peak of a first ring member and a peak of an adjacent ring member and at least one bridge member extending between a valley of a first ring member and a valley of an adjacent ring member. The peak-peak bridge members alternate with the valley-valley bridge members along successive circumferential rows along a longitudinal axis of the tubular stent. The ring members each have a plurality of substantially linear strut members with opposing ends of each of the substantially linear strut members begin contiguous with one of a peak or a valley of the circumferential ring member.

The alternative variants differ from each other in one or more of the following general aspects: 1) configuration of the radiopaque markers; 2) surface topography the outer surface of the stent; and/or 3) presence or absence of a drug coating on the outer surface of the stent. The embodiments of the peripheral below-the-knee stent of the present invention include the following:

i. stent having proximal and distal projections and radiopaque materials coupled to the proximal and distal projections;
  ii. stent having proximal and distal projections, radiopaque materials coupled to the projections, and volume-enhancing features on an outer or abluminal surface of the stent;
  iii. stent having proximal and distal projections, radiopaque materials coupled to the projections, volume-enhancing features on the abluminal surface of the stent, and a drug coating on the abluminal stent surface and in the volume-enhancing features;
  iv. stent having no proximal and distal projections and radiopaque materials coating only low-stress regions of the abluminal surface of the stent;
  v. stent having no proximal and distal projections, volume-enhancing features on the abluminal surface of the stent, and radiopaque materials coating low-stress regions of the abluminal surface of the stent and in the volume-enhancing features;
  vi. stent having no proximal and distal projections, radiopaque materials coating low-stress regions of the abluminal surface of the stent, and volume-enhancing features in the radiopaque material on the abluminal surface of the stent;
  vii. stent having no proximal and distal projections, volume-enhancing features on the abluminal surface of the stent, radiopaque materials coating low-stress regions of the abluminal surface of the stent, and a drug coating over the radiopaque materials coating, the abluminal surface of the stent and in the volume-enhancing features; and/or
  viii. stent having no proximal and distal projections, radiopaque materials coating low-stress regions of the abluminal surface of the stent, volume-enhancing features in the radiopaque material on the abluminal surface of the stent, and a drug coating over the radiopaque materials coating, over the abluminal surface of the stent and in the volume-enhancing features.

In a first embodiment of the invention, the stent includes a plurality of projections at each of the proximal and distal end of the stent. Each of the projections is contiguous with a peak of a terminal circumferential ring of the stent. Each of the projections comprises a frame defining a central open region. A radiopaque cuff is joined to each of the plurality of projections and covers the central open region. The radiopaque cuff preferably wraps around and is secured to the frame of each projection.

In a second embodiment of the invention, the stent does not include a plurality of projections at each of the proximal and distal ends of the stent. Rather in the second embodiment, a radiopaque layer is coated onto an outer surface of the stent only at low-stress regions of the stent. The low-stress regions of the stent are typically the strut regions of the stent between the peaks and the valleys and not on the peaks and valleys or on the bridge members.

In a third embodiment of the invention, the stent has a drug-eluting coating on the outer surface of the stent, with the stent being either the first embodiment or the second embodiment described above.

In a fourth embodiment of the invention, either the first or second embodiments of the stent, as described above, may be employed. A plurality of surface volume-enhancing features, such as, for example, elongate grooves, are formed in or on the outer surface of the stent about at least a substantial extent of the stent's entire length. The plurality of volume-enhancing features are preferably oriented generally parallel to the longitudinal axis of the stent when the stent is in its diametrically expanded state. The plurality of volume-enhancing features may, optionally, also be formed in the plurality of projections and radiopaque cuff in accordance with the first embodiment of the invention. Optionally, the plurality of volume-enhancing features may be formed in the outer surface of the stent prior to coating the stent with the radiopaque material in accordance with the second embodiment of the invention described above.

In a fifth embodiment of the invention, the third and fourth embodiments are combined such that the stent has a plurality of volume-enhancing features in or on either the outer surface of the stent or in the outer surface of the radiopaque coating and has a drug-eluting coating on the outer surface of the stent and/or the outer surface of the radiopaque coating. At least a portion of the drug elution coating is disposed within the volume-enhancing features. Those skilled in the art will appreciate that the volume-enhancing features or grooves provide additional surface volume to the stent and, therefore, accommodates a greater volume of the drug-eluting coating and, hence, a greater quantity of the drug than would be present with a drug-eluting coating when compared to a stent having a non-grooved surface.

In a sixth embodiment of the invention, the stent in accordance with any of the first, second, third, fourth and fifth embodiments is provided, with the stent having a hybrid structure of open cells, with a first open cell geometry positioned at proximal and distal ends or regions of the stent and a second open cell geometry begin present at an intermediate region of the stent.

In a seventh embodiment of the invention, a planar mask having an elongate opening is provided for coating the outer surface of a stent with a radiopaque material.

In an eighth embodiment of the invention, a cylindrical mask having a plurality of elongate openings is provided for coating the outer surface of a stent with a radiopaque material.

In a ninth embodiment of the invention, a stent delivery system is provided. The delivery system comprises, generally, a catheter onto which the inventive sent is mounted toward a distal end of the catheter, an atraumatic tip at the distal end of the catheter, a sheath concentrically engaged about the catheter and configured to enclose the stent between the catheter and the sheath during delivery, a handle coupled to both the catheter and the sheath and having a retraction mechanism operably coupled to the sheath. Actuation of the retraction mechanism, retracts the sheath proximally into the handle, thereby exposing the stent for delivery to a desired site within a body.

The foregoing general descriptions of the variants of the invention will be described in greater particularity with reference to the accompanying Figures.

Figure 2:
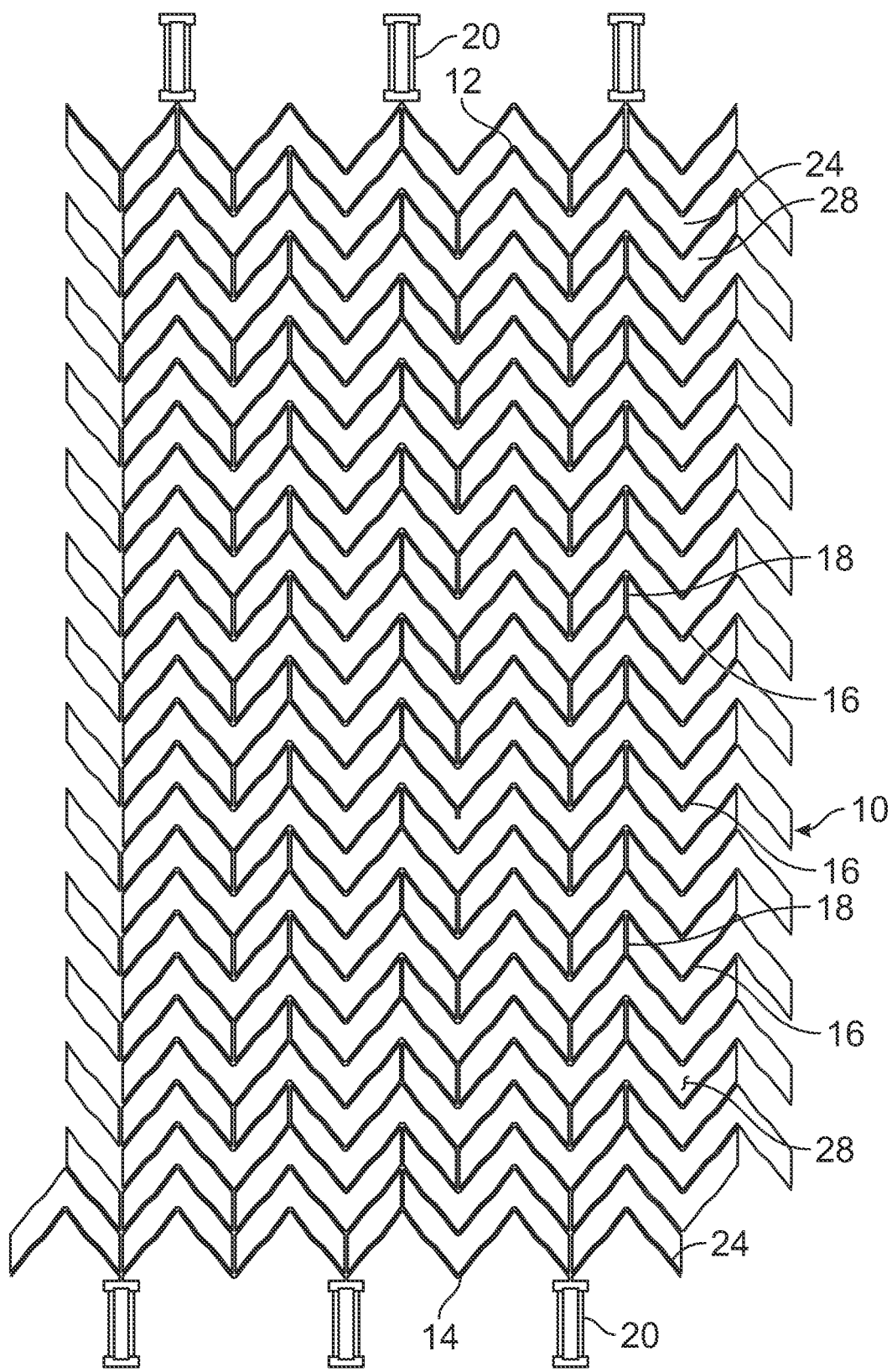
FIG. 2 is a flat view of the stent in accordance with the first embodiment of the present invention.

Turning to FIGS. 1 and 2, the inventive peripheral below-the-knee stent 10 is shown. In accordance with the first embodiment of the invention, stent 10 is a tubular member having a first end 12 and a second end 14 corresponding to the proximal and distal ends of the stent. Stent 10 also has a longitudinal axis L and a circumferential axis C. Stent 10 is composed of a plurality of rings 16 extending about the circumferential axis C of stent 10. Laterally adjacent pairs of rings 16 are interconnected by at least one of a plurality of bridge members 18. Each of the rings 16 has a sinusoidal configuration with a plurality of peaks 32 and valleys 40. One of the plurality of bridge members 18 interconnects a peak 40 of one ring 16 to a valley 32 of a second adjacent ring 16. More than one bridge member 18 preferably interconnects adjacent rings 16 about their circumference. The bridge members 18 support adjacent rings 16 in a spaced apart relationship and define a plurality of cells 24, 28 in the space bounded by the bridge members 18 and sections of the rings 16.

In each of the embodiments of the stent of the present invention, each of the plurality of bridge members 18 are substantially linear and, optionally, may have a taper in either width and/or thickness at an end of the bridge member 18 that connects to a valley 32. This taper will aid in bend flexibility of the stent 10.

The cells 24, 28 are preferably a hybrid of different open cell geometries. As is known in the stent arts, closed-cells are characterized by small free cell areas between struts and bridge members and are constrained from longitudinal flexion about their entire free cell area. In contrast, open-cells have relatively larger free cell areas between struts or bridge members and have unconstrained regions of the free cell area. For purposes of the present application, reference to cell shape or cell area will be made based upon their shape or area when the stent is in its diametrically expanded state. Cells 24, 28 are open regions defined between longitudinally adjacent rings 16 and extending about the circumferential axis of the stent 10. The bridge members 18 delimit circumferentially adjacent cells 24, 28.

Figure 3:
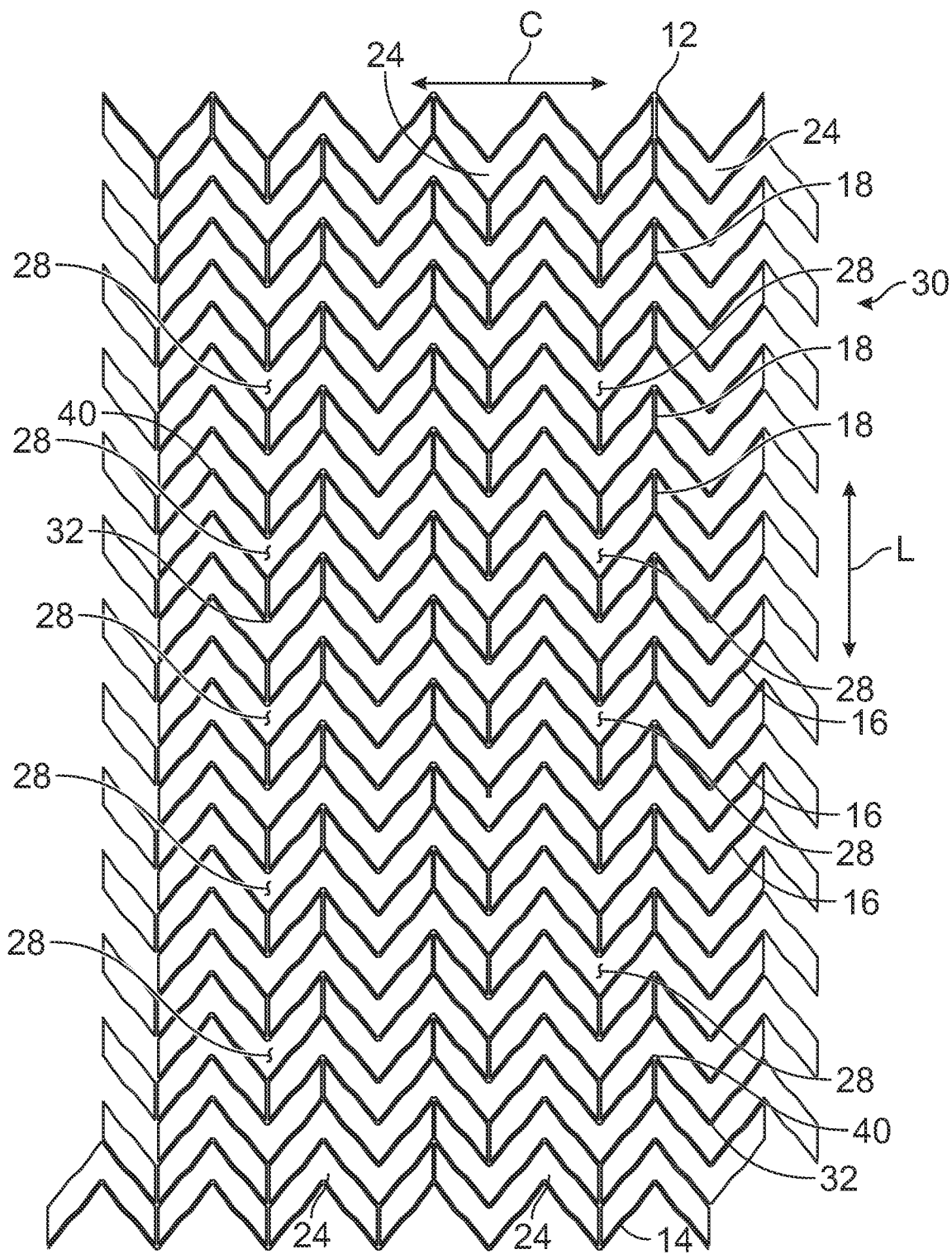
FIG. 3 is a flat view of a stent in accordance with a second embodiment of the present invention.
Figure 4:
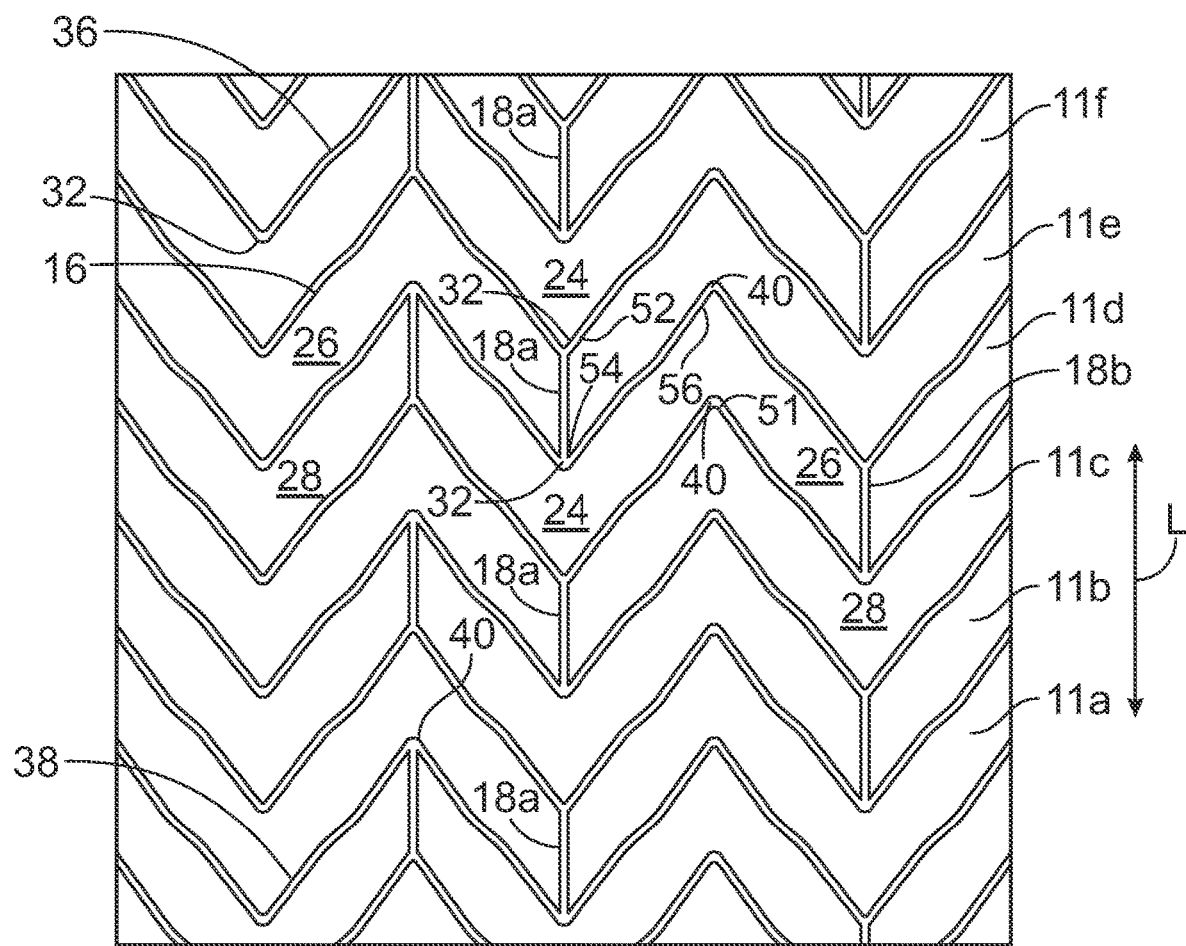
FIG. 4 is a fragmentary plan view of the stent in accordance with the first and second embodiments of the present invention.
Figure 7:
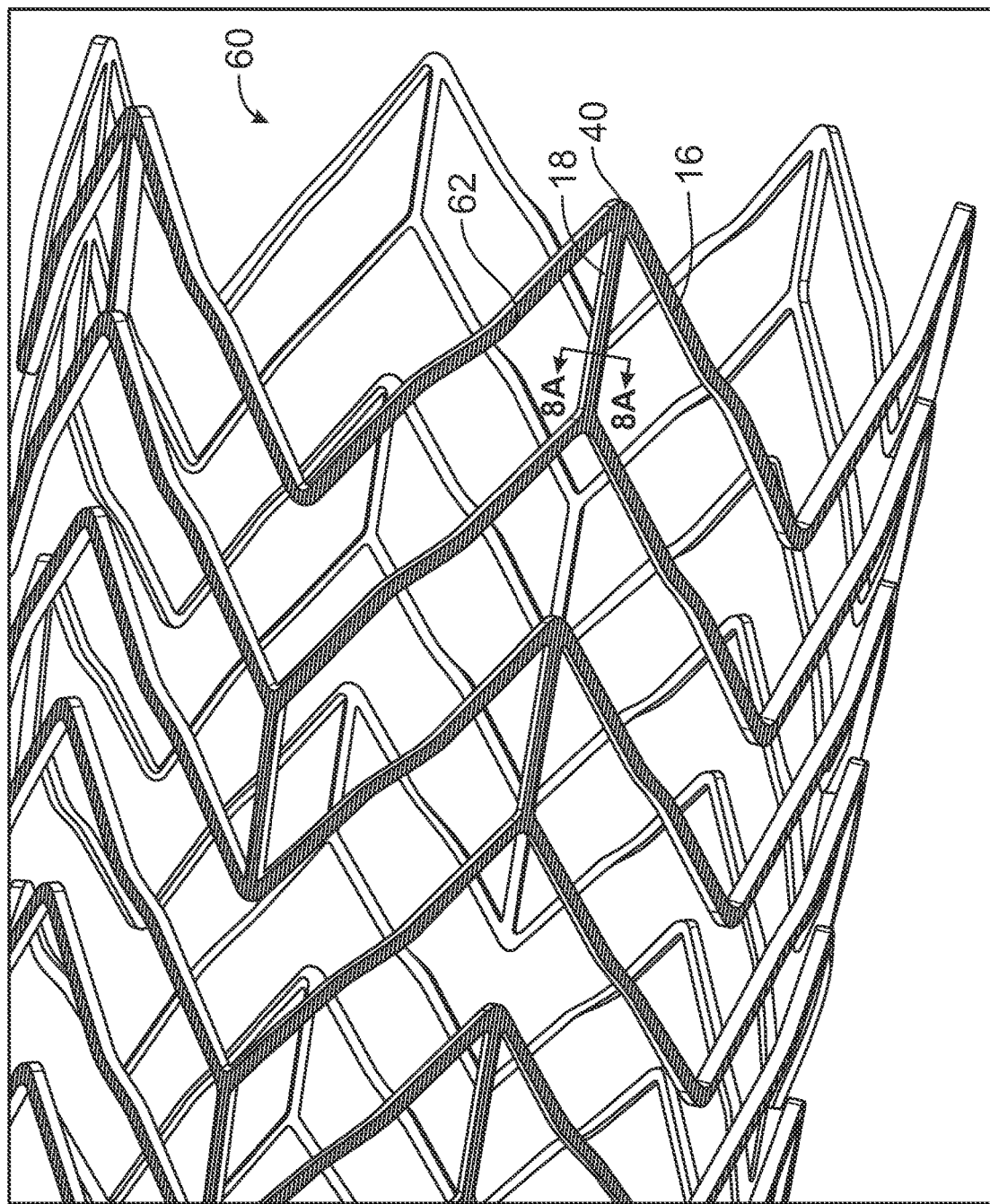
FIG. 7 is a perspective view of a terminal end portion of an inventive stent in accordance with a third embodiment of the present invention.
Figure 8A:
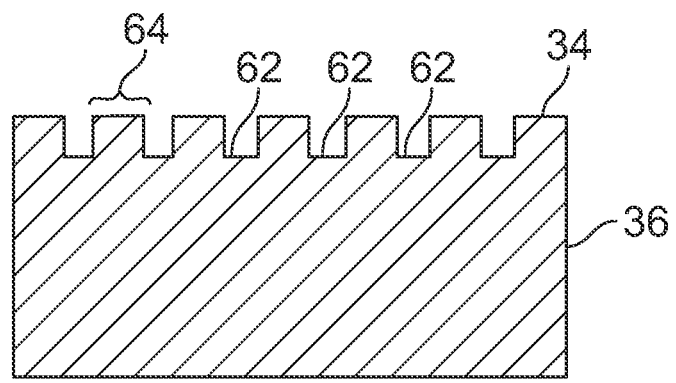
FIG. 8A is a cross-sectional view taken along line 8A-8A of FIG. 7.
Figure 8B:
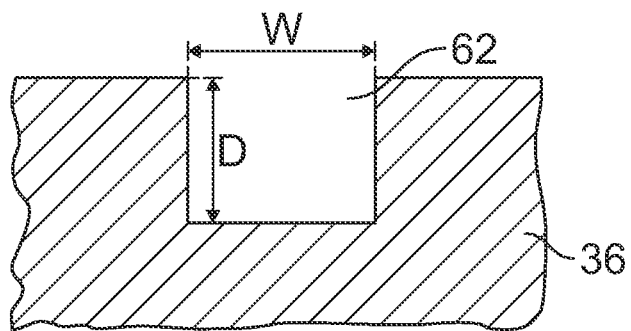
FIG. 8B is a fragmentary view of a section of FIG. 8A.

In accordance with the first embodiment of stent 10, as depicted in FIGS. 1 and 2, or in accordance with the second embodiment of stent 30, depicted in FIG. 3, and in the enlarged view of FIG. 4, first cell 24 is an open cell having a substantially V-shape and second cell 28 is an open cell having a generally Z-shape. The substantially V-shaped first cells 24 are positioned at each of the proximal end 12 and the distal end 14 of the stent 10, 30, while the substantially Z-shaped second cells 28 are positioned along an intermediate region 26 of stent 10, 30. This arrangement of open cells 24, 28 lends high degrees of longitudinal flexibility and radial expandability to the stent 10, 30.

The stents 10, 30 of the present invention have a wall thickness between about 50 μm and about 100 μm, with the wall thickness preferably between about 75 μm to about 95 μm. The wall thickness is ideally generally uniform about the longitudinal axis and circumferential axis of the stent 10, 30. The stents 10, 30 have an expansion ratio of up to about 6.4:1 and are capable of being crimped to an outer diameter of about 0.84 mm outer diameter and radially expand up to an outer diameter of about 5.4 mm. The crimped diameter of about 0.84 mm allows for use of a 3.5 French delivery catheter sheath, which is well suited to percutaneous delivery through pedal access. Those skilled in the art will understand that the foregoing dimensions, ratios, sizes and other values are exemplary and that other wall thicknesses, expansion ratios, crimp diameters, expansion diameters, delivery sheath sizes and the like are also intended by the present invention.

Stents 20, 30 are preferably made of shape memory alloy and/or superelastic alloy. As noted above, shape memory and/or superelastic alloys may be binary, ternary, quaternary, quinary or n-ary, where n-is an integer of the base value metal alloys. While binary nickel-titanium alloys are well known in the art, other alloy additions of platinum, palladium, tantalum, tungsten, zirconium, hafnium and/or gold may also be used. Further, it is preferably that the stents 20, 30 be made by physical vapor deposition of shape memory alloy and/or superelastic alloy materials onto a cylindrical mandrel to form a stent hypotube on the cylindrical mandrel. The stent 20, 30 pattern geometry then preferably laser cut into the stent hypotube and then removed from the cylindrical mandrel.

Physical vapor deposition of shape memory alloys and/or superelastic alloys onto cylindrical mandrels is known in the art. Such processes are exemplified by U.S. Pat. Nos. 6,379,383, 7,335,426, 9,640,359, each of which are hereby incorporated by reference.

The second embodiment of the stent 30 is illustrated with reference to FIG. 3. Stent 30 has the same structure of rings 16 and bridge members 18, but lacks the proximal and distal projections 20 or radiopaque cuffs 22 coupled to the proximal and distal projections 20. Instead of the proximal and distal projections 20 and radiopaque cuffs, stent 30 has a coating of radiopaque material on portions of the outer or abluminal surface of the stent 30 as will be described in greater detail with reference to FIG. 9 hereinafter. Like stent 10, stent 30 is made of a shape memory or superelastic material.

As best seen in FIG. 4, each peak 40 has an innermost part 56 and an outermost part 57 of the peak 40. The innermost part 56 of peak 40 lies on a lateral surface of the ring member 16 and is positioned in the included angle formed by the adjacent struts 36 of which the peak 40 is the vertex. The outermost part 57 of peak 40 lies on an opposing lateral surface of the ring member 16 as the innermost part 56 and is positioned at the vertex of peak 40. Similarly, an innermost part 54 of valley 32 lies on a lateral surface of the ring member and is positioned in the included angle formed by the adjacent struts 36 of the valley 32. An outermost part 52 of valley 32 lies on an opposing lateral surface of the ring member as the innermost part 54 and is positioned at the vertex of the valley 32.

Again, as best illustrated in FIGS. 2 and 4, each ring 16 is comprised of generally linear strut members 36 that extend in a generally helical axis, with either a right-handed or a left-handed orientation relative to the longitudinal axis L, of the stent 10, 30 and between a peak 40 and a valley 32 on each of the plurality of rings 16. In this manner, the sinusoidal shape of each ring 16 is formed. Optionally, the strut members 36 may be provided with an offset section 38, as best illustrated in FIG. 4, present at an intermediate point along a length of the strut members 36. The offset section 38 is preferably a lateral offset along the circumferential axis of the stent 10. Offset section 38 allows adjacent rings 16 to nest relative to each other and assists in allowing for the very low crimped profile and low crossing profile of the stent embodiments during delivery.

A first set of bridge members 18a interconnect an outermost portion 52 of a valley 32 with an innermost portion 54 of a valley 32 on an adjacent ring 16, while a second set of bridge members 18b interconnect an innermost portion 56 of a peak 40 with an outermost portion 58 of an adjacent ring 16. Optionally, and preferably, the bridge members of the first set of bridge members 18a are in alignment with along the longitudinal axis of the stent 10, 30 while the bridge members of the second set of bridge members 18b are in alignment with the longitudinal axis of the stent 10, 30.

As noted above, adjacent rings 16 are maintained in spaced apart relationship by bridge members 18. Adjacent rings 16 are in substantially synchronous alignment such that the peaks 40 and valleys 32 of adjacent pairs of rings 16 are in substantial alignment about both the circumferential axis C and longitudinal axis L of stent 10, 30. In this manner, a plurality of rows 11 are formed between adjacent rings 16 along the longitudinal axis of the stent 10, 30. As best illustrated with reference to FIG. 4, the plurality of rows 11 are denoted as rows 11a, 11b, 11c, 11d, 11e and 11f. While only a few rows are illustrated in the enlarged fragmentary view of FIG. 4, those skilled in the art will appreciate, as illustrated in FIGS. 1-3, that the plurality of rows 11 extend along the entire longitudinal axis of the stent 10, 30 ending only with the terminal rings 16 at the first end 12 and second end 14 of the stent 10, 30.

Rows 11 are the circumferential spaces between longitudinally adjacent rings 16 and include the bridge members 18 that maintain spacing between the longitudinally adjacent rings 16 forming each row 11. The first set of bridge members 18a and the second set of bridge members 18b are in circumferentially spaced apart relationship relative to one another and staggered in alternating rows 11. This staggered relationship of the first set of bridge members 18a and the second set of bridge members 18b is illustrated in FIG. 4 wherein the first set of bridge members 18a are in row 11a and the second set of bridge members 18b are in row 11b and are circumferentially offset from the first set of bridge members 18a. The first set of bridge members 18a are generally aligned along the longitudinal axis L of the stent 10, 30 and staggered in alternating rows 11. As illustrated in FIG. 4, first set of bridge members 18a are found in rows 11a, 11c and 11e. Similarly, the second set of bridge members 18b are generally aligned along the longitudinal axis L of the stent 10, 30 and are staggered in alternating rows 11. Also as illustrated in FIG. 4, second set of bridge members 18b are found in rows 11b, 11d and 11f. These staggered patterns of bridge members 18 along the longitudinal axis L and offset patterns of bridge members 18 about the circumferential axis C of stent 10, 30 are repeated along the entire intermediate section 26 of stent 10, 30.

In accordance with all embodiments of the stent 10, 30 of the present invention, the terminal end rows 11 at each of the first end 12 and the second end 14 of the stent 10, 30 are optionally configured as a circumferential series of V-shaped first open cells 24. As illustrated in FIGS. 2, 3 and 5, the V-shaped open cells 24 are formed by adjacent rings 16 synchronously positioned with peak 40 to peak 40 and valley 32 to valley 32 alignment in the longitudinal axis L of the stent 10, 30. Bridge members 18 interconnect adjacent peaks 32 and adjacent valleys 40 in the adjacent rings 16.

The above-described hybrid combination of first open cells 24 and second open cells 28 having different open cell geometries, in combination with the shape memory or superelastic alloy construction of stent 10, 30, lends both column and radial strength and longitudinal flexibility to the stent 10, 30. These attributes are crucial to achieve high expansion ratios of up to or greater than 6:1, crush resistance to at least about 90% of the expanded diameter of the stent, a stent having a crimp diameter down to about 0.85 mm for low-crossing profile delivery compatible with a 3.5 French delivery system suitable for pedal access, and a uniform radial strength of at least about 0.5 N/mm along the stent's entire circumference and length. These features of the stent 10, 30 are all present where the stent 10, 30 has a wall thickness between about 50 to about 100 μm, more particularly between about 60 μm to about 90 μm and even more particularly between about 75 μm and about 95 μm, and stent 10, 30 lengths up to about 200 mm.

Physical vapor deposition of the shape memory or superelastic alloy of the stent 10, 30 creates a stent material that is characterized by having at least 200% fatigue resistance and higher corrosion resistance when compared with stents fabricated from the same shape memory or superelastic materials made by wrought material processing, which require secondary passivation to achieve acceptable fatigue and corrosion resistance.

One of ordinary skill in the art is able to readily derive and compare corrosion resistance and fatigue resistance of both the inventive stent and stents made from wrought materials without the exercise of routine experimentation. Ample guidance is available to measure corrosion and fatigue resistance, as well as axial and radial strength and crush resistance with reference to both regulatory guidance and standard test methodologies. For example, corrosion resistance for stents may be determined by ASTM F2129-17b, Standard Test Method for Conducting Cyclic Potentiodynamic Polarization Measurements to Determine the Corrosion Susceptibility of Small Implant Devices, ASTM International, West Conshohocken, PA, 2017, www.astm.org. Fatigue resistance for stents may be determined by ASTM F2477-07(2013), Standard Test Methods for in vitro Pulsatile Durability Testing of Vascular Stents, ASTM International, West Conshohocken, PA, 2013, www.astm.org and/or ASTM F2942-13, Standard Guide for in vitro Axial, Bending, and Torsional Durability Testing of Vascular Stents, ASTM International, West Conshohocken, PA, 2013, www.astm.org. The United States Food and Drug Administration has also issued a Guidance for Industry and FDA Staff entitled *Non-Clinical Engineering Tests and Recommended Labeling for Intravascular Stents and Associated Delivery Systems* (Apr. 18, 2010) and *Select Updates for Non-Clinical Engineering Tests and Recommended Labeling for Intravascular Stents and Associated Delivery Systems* (Aug. 18, 2015) both of which provide guidance on corrosion and fatigue testing for stents and are hereby incorporated by reference.

When the inventive stent 10, 30 is compared with the ZILVER (Cook Medical) stent, as illustrated in FIGS. 5 and 6, the ZILVER stent has a single open cell geometry that is uniform throughout the stent. As illustrated in FIG. 5, the ZILVER stent has a generally WV-shaped open cell geometry, shaded for reference that is consistent along the entire length of the stent. Moreover, the ZILVER stent has peaks and valleys with enlarged widths that accommodate connection with the bridge members relative to the peaks and valleys that are not connected by bridge members. In contrast, the inventive stent 50 has a hybrid open cell geometry with the first open cells 24 having a generally V-shape and the second open cells 28 having a generally Z-shape, both are shaded for reference.

The basic geometry of stent 10, 30 as described above is common to all the following embodiments, which differ only in i) presence or absence surface topographical features; ii) presence or absence of a drug coating; and/or iii) presence or absence of proximal and distal projections.

Turning to FIGS. 7-10 in the accompanying Figures there is depicted embodiments of the stent 60 having a plurality of volume-enhancing features 62, such as elongate grooves, formed in the outer surface of the stent 60. The volume-enhancing features 62 are preferably, but not necessarily, formed in the entire outer surface of the stent 60, including the rings 16 and the bridge members 18. As an alternative to the volume-enhancing features 62 being formed in or on the outer surface of the stent 60, the volume-enhancing features 62 may be formed in or on an outer surface of a radiopaque coating which is coated onto the outer surface of the stent, as will be described in greater detail hereinafter. Thus, the volume-enhancing features 62 may be formed in the outer surface of the stent 60 or in the outer surface of a radiopaque layer which, itself, is immediately adjacent the outer surface of the stent 60.

The volume-enhancing features 62 may have virtually any transverse cross-sectional shape including, without limitation, V-shape, U-shape, keyhole-shape, or the like. While volume-enhancing features 62 are shown as linear grooves in FIG. 7, the volume-enhancing features 62 may also be sinusoidal, meander or have other curvilinear shapes along the longitudinal axis L of the stent 60. The volume-enhancing features 62 each have a width W and a depth D. Depth D and width W may have the same value, e.g., 10 μm depth, 10 μm width, or may have different values, e.g., 10 μm depth, 5 μm width. Adjacent grooves 62 further have an inter-groove spacing 64 which is a distance between the adjacent grooves 62. The inter-groove spacing 64 may either be measured edge to edge or center to center of the adjacent grooves 64. The inter-groove spacing 64 may be greater than or equal to the groove 62 width W or, alternatively, may be less than or equal to groove 62 width W. The volume-enhancing feature 62 may have a width to depth ratio been about 1:1 to about 1:3. The use of the term "groove" intended to be construed as a channel or depression; a notch or indentation that does not pass entirely through the thickness of the material in which the groove is present.

The volume-enhancing features 62 of the present invention are configured to add between about 20% to about 80% more surface volume to the outer or abluminal surface of the stent. Those skilled in the art will understand that the degree of added surface volume is a function of the geometry, spacing, width and depth of the volume-enhancing features 62 on the surface of stent 60.

Vesga, B., et al., demonstrated that the presence of microgrooves on the luminal surfaces of a MULTI-LINK VISION (Abbott Vascular, Santa Clara, CA) bare metal coronary stent exhibited significantly lower levels of neointimal proliferation and greater mature neointima at a faster rate when compared to flat non-grooved surfaces in humans. Vesga, B., et al. Open Heart 2017; 4:e00052. Doi:10.1136/openhrt-2016-000521. Methods of forming the microgrooves on the luminal stent surfaces are found in U.S. Pat. No. 8,512,579, which are hereby incorporated by reference.

Figure 9:
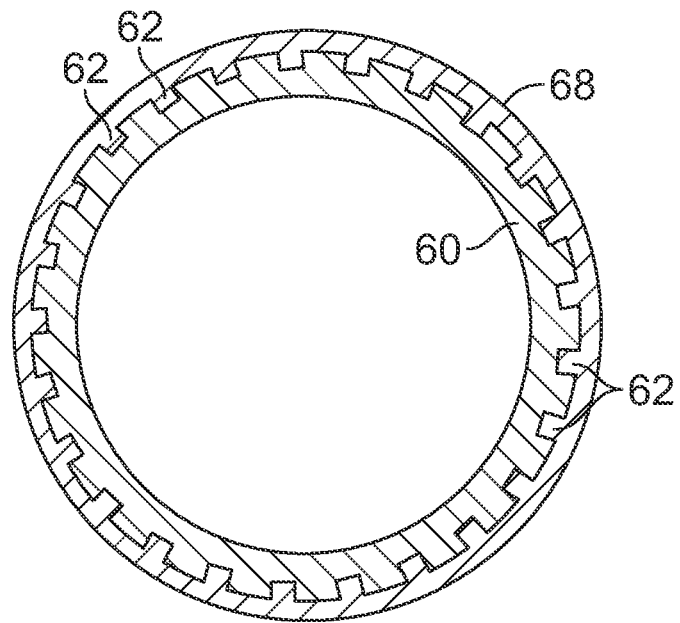
FIG. 9 is a diagrammatic cross-sectional view of a fourth embodiment of the inventive stent.
Figure 10:
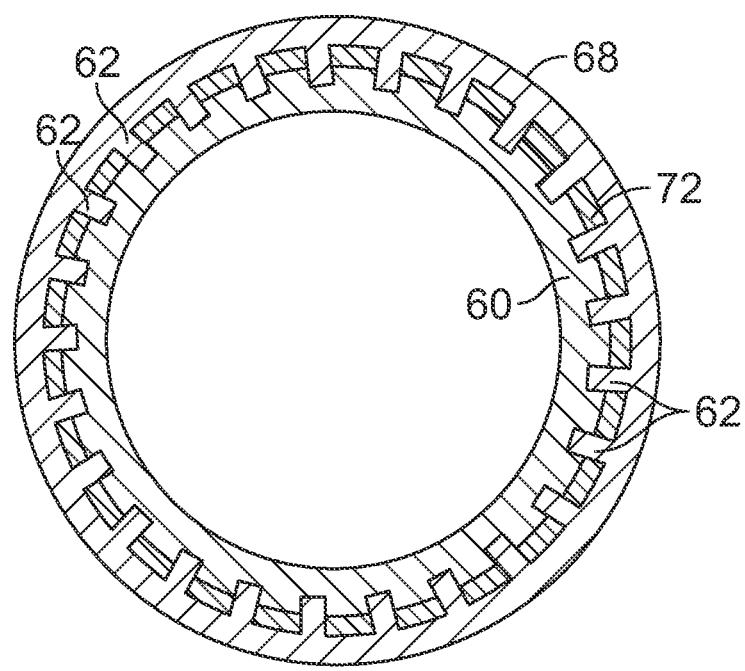
FIG. 10 is a diagrammatic cross-sectional view of a fifth embodiment of the inventive stent.
Figure 11:
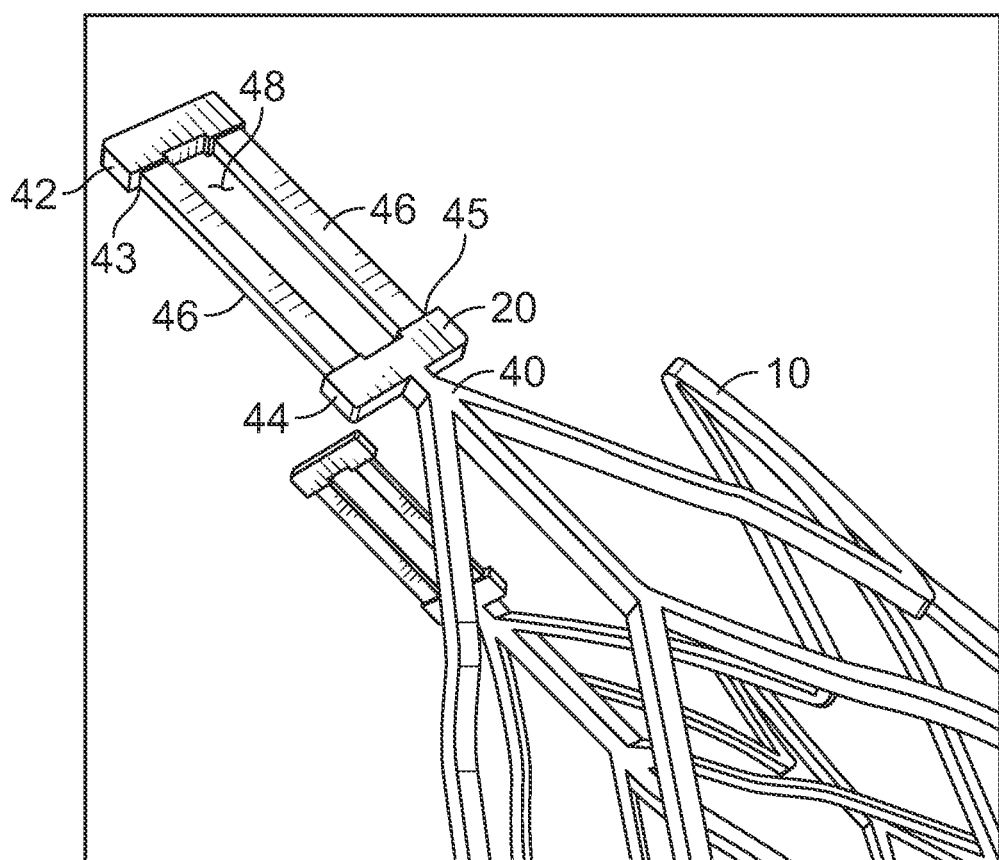
FIG. 11 is a fragmentary perspective of a terminal end portion of the stent in accordance with the first embodiment of the present invention.
Figure 12:
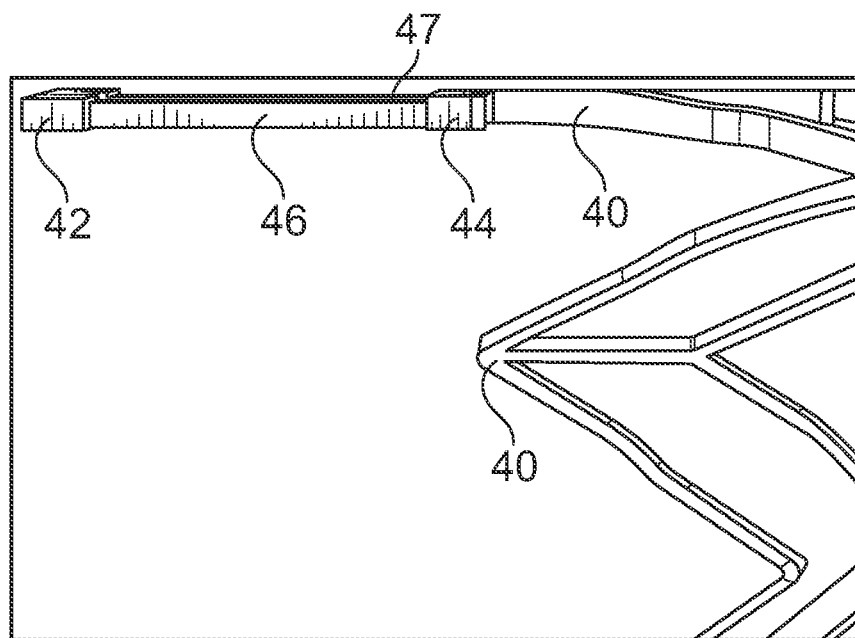
FIG. 12 is a fragmentary side elevational view of the end portion of the stent in accordance with the first embodiment of the present invention.
Figure 13:
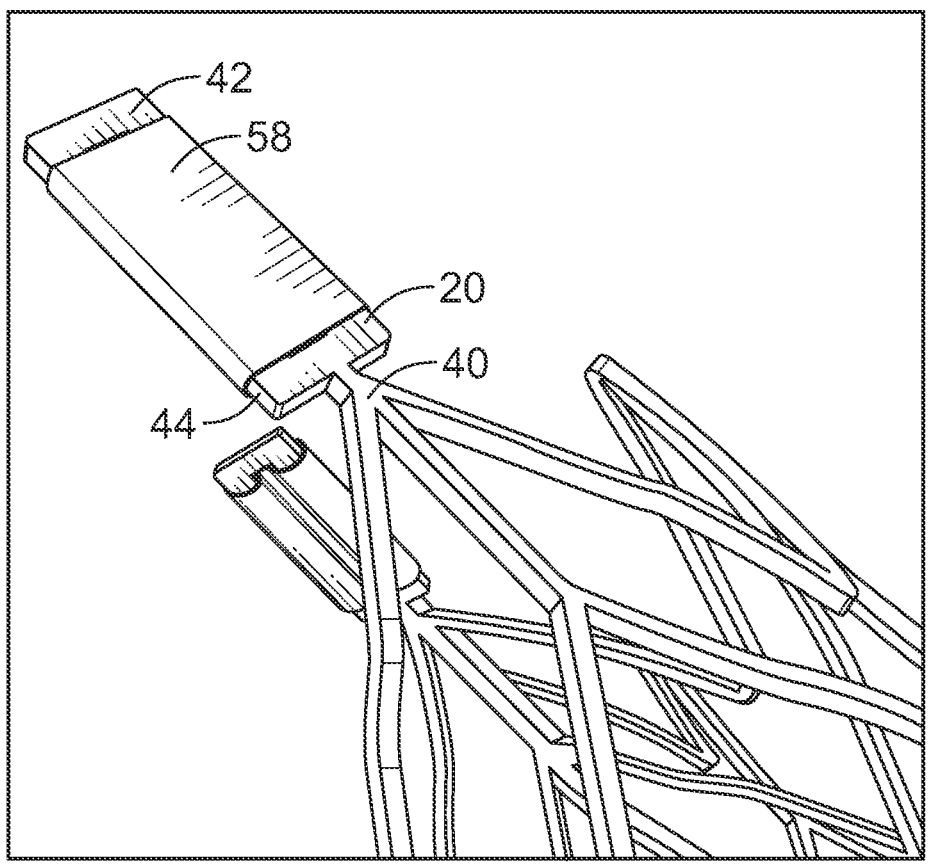
FIG. 13 is a fragmentary plan view of the end portion of the inventive stent illustrating a radiopaque marker affixed to the end portion in accordance with the first embodiment of the present invention.
Figure 14:
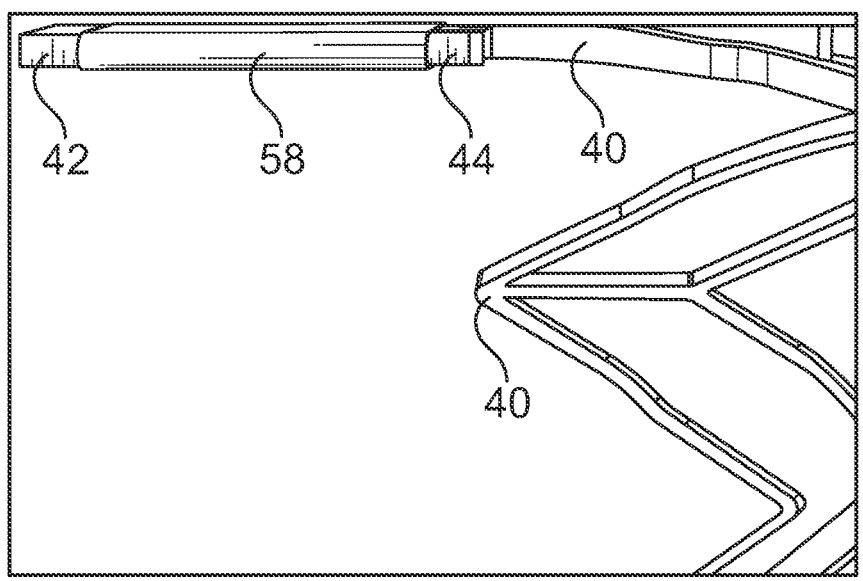
FIG. 14 is a fragmentary side elevational view of the end portion of the stent illustrating a radiopaque marker affixed to the end portion in accordance with the first embodiment of the present invention.

Unlike the grooves on the luminal surface of a coronary stent, as described in Vesga, B. et al. or U.S. Pat. No. 8,512,579, the grooves 62 of the present invention are present in the outer surface 35 of the stent 60. In accordance with one embodiment of the invention, as illustrated in FIG. 9, stent 60 has a plurality of grooves 62 formed in its outer surface 34 and a drug eluting coating 68 covering the outer surface 34 of the stent 60 and at least partially filling each of the plurality of grooves 62. Regardless of the depth D and width W of the grooves 62 and regardless of the inter-groove spacing 64, the presence of the grooves 62 serves to increase the available surface volume for the drug eluting coating 68 when compared to a non-grooved surface. It is within the ordinary skill of one in the art through routine experimentation to determine the desired depth D, width W and inter-groove spacing 64 based upon any given specific stent design. Further, one skilled in the art will understand and appreciate that at the position of any given groove 62, the thickness of the drug eluting coating 68 is greater than the thickness of the drug eluting coating covering the inter-groove surfaces of the stent 60. For example, the drug eluting layer may substantially fill the plurality of grooves and have a thickness of between about 3 µm to about 20 µm from the outer abluminal surface of the stent. The increase thickness of the drug eluting coating 68 in the regions of the grooves 62 not only increases the amount of drug capable of eluting from those groove 62 regions, but also increases the elution time profile overall when compared to non-grooved stent surfaces.

For example, where an individual groove 62 has a width of 10 µm, a depth of 10 µm and a length of 10 mm, for example on an individual bridge member 18 having a length of 10 mm, the groove 62 provides an additional volume of 1.0 $mm^3$. Where there are three grooves 62 on an individual bridge member 18, the total additional volume is 3.0 $mm^3$ when compared to a non-grooved surface for a single individual bridge member 18.

Where the drug eluting coating 38 has a thickness of about 3-5 µm from the outer surface 34 of the stent 60, not including the depth of the grooves 62, the drug eluting coating 38 will have a thickness of about 10 µm when measured from the bottom surface of the grooves 62.

Alternatively, the stent 60 may be provided with grooves 62 and without the drug coating 38 to provide a bare metal grooved stent, with the grooves 62 on the outer surface 34 of the stent 60.

Turning to FIGS. 11-14 in which the end projections 20 are illustrated in greater detail. End projections 20 extend from an outermost portion 57 of peak 40 and serve as a platform for attaching a radiopaque marker. In accordance with an embodiment of the present invention, the end projections 20 may be a quadrilateral frame defining a central open space 48. The frame has a first end frame member 44 that is coupled to peak 40 and a second end frame member 44 at an opposing end of the end projection 20 and in spaced apart relationship to the first end frame member 44. Lateral frame members 46 extend between the first end frame member 44 and the second end frame member 42 and are in spaced apart relationship with one and other. The central open space 48 is bounded on its lateral aspects by the lateral frame members 46 and on its end aspects by the first end frame member 44 and the second end frame member 42. The lateral frame members 46 are preferably thinner in wall thickness than the first end frame member 44 and the second end frame member 42 and are inset from outer lateral edges thereof, thereby defining a first recess 45 and a second recess 43 relative to the outer lateral edges of the first end frame member 44 and the second end frame member 42. Similarly, by having a thinner wall thickness than the first end frame member 44 and the second end frame member 42, the lateral frame members also define a third recess 47 by this differential thickness.

A radiopaque cuff member 58 is coupled to the end projection 20. The radiopaque cuff member 58 may be a tubular member that is flattened or crimped onto the end projection 20 or it may be a planar member that is wrapped around and secured to the end projection 20. The radiopaque cuff member 58 seats within and against first recess 45, second recess 43 and third recess 47 and covers and at least substantially encloses the open space 48 in the end projection 20. Preferably, the radiopaque cuff member 58 has a thickness selected to correspond to depths of the first recess 45, second recess 43 and third recess 47 such that an outer surface of the radiopaque cuff member 58 lies substantially co-planar with outer surfaces of the first end frame member 44 and the second end frame member 42.

The outer surfaces of the first end frame member 44 and the second end frame member are preferably co-planar with the outer surface 34 of the stent 10. Similarly, the inner surfaces of the first end frame member 44 and the second end frame member are preferably co-planar with the inner or luminal surface of the stent 10. The first end frame member 44, the second end frame member 42, and/or the radiopaque cuff 58 may also have grooves 62 formed in surfaces thereof Similarly, the first end frame member 44, the second end frame member 42, and/or the radiopaque cuff 58 may also have grooves 62 formed in surfaces thereof and may have the drug eluting coating 68 over the outer surfaces thereof and at least partially filling the grooves 62 formed in surfaces thereof.

Figure 15A:
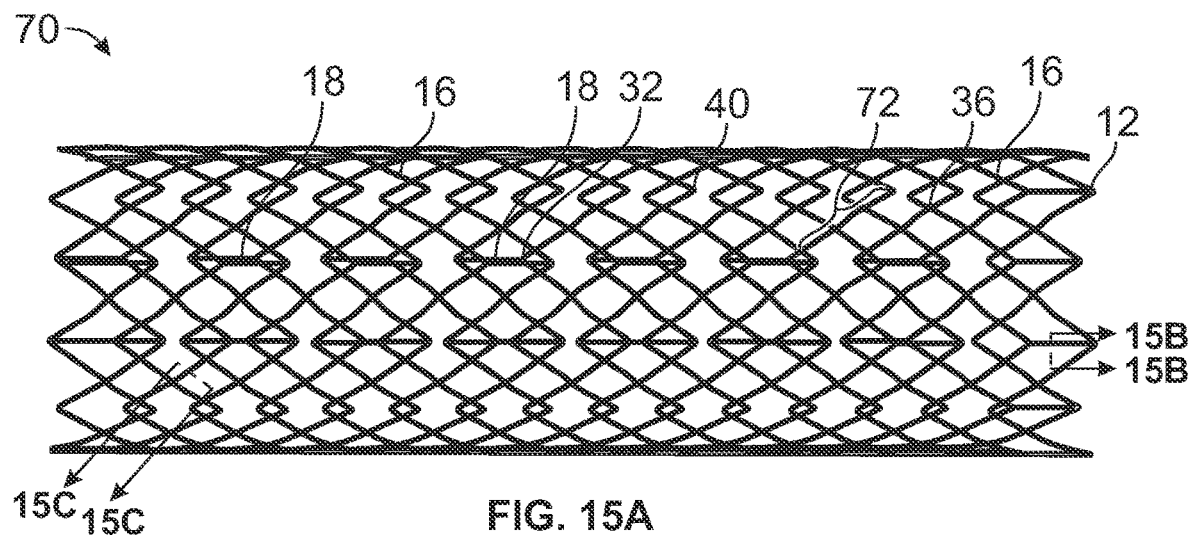
FIG. 15A is a side elevational view of a portion of the stent in accordance with a sixth embodiment of the present invention.
Figure 15B:
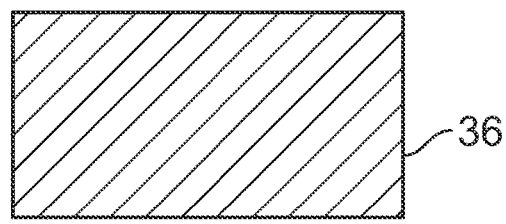
FIG. 15B is a cross-sectional view taken along line 15B-15B of FIG. 15A.
Figure 15C:
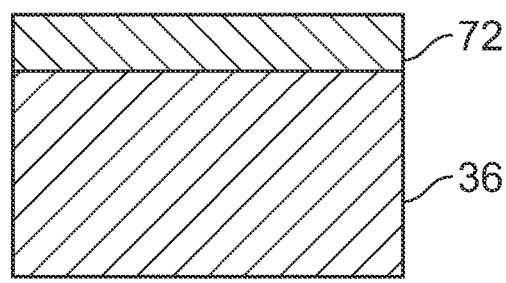
FIG. 15C is a cross-sectional view taken along line 15C-15C of FIG. 15A.

FIG. 15 depicts a variant of the stent 10, 30 of the present invention which consists of radiopaque coated stent 70. Radiopaque coated stent 70 is identical in structure with stent 30, i.e., having sinusoidal rings 16 interconnected by bridge members 18, having hybrid open cell structure with first open cells 24 with a generally V-shape at the first end 12 and the second end 14 (not shown) and second open cells 28 having a generally Z-shape along the intermediate section of radiopaque coated stent 70 and being without end projections 20. Radiopaque stent 70 has the addition of a radiopaque coating 72 on the outer surface 34 of the radiopaque coated stent 70. Radiopaque coating 72 is preferably present only on low-stress or low-strain regions of the radiopaque coated stent 70 and forms a discontinuous partial coating along the longitudinal axis L of the radiopaque coated stent 70. As illustrated in FIG. 15, the radiopaque coating 72 is present only on intermediate sections of the struts 36 and not present on the struts at the peaks 40, valleys 32 or bridge members 18 of the radiopaque coated stent 70. By forming a discontinuous partial coating of the radiopaque coating 72 on only the low-stress or low-strain regions of the radiopaque coated stent 70, risk of delamination of the radiopaque coating 72 from the outer surface 34 of the stent 70 during crimping and/or radial expansion of the stent 70 is significantly reduced.

Figure 16:
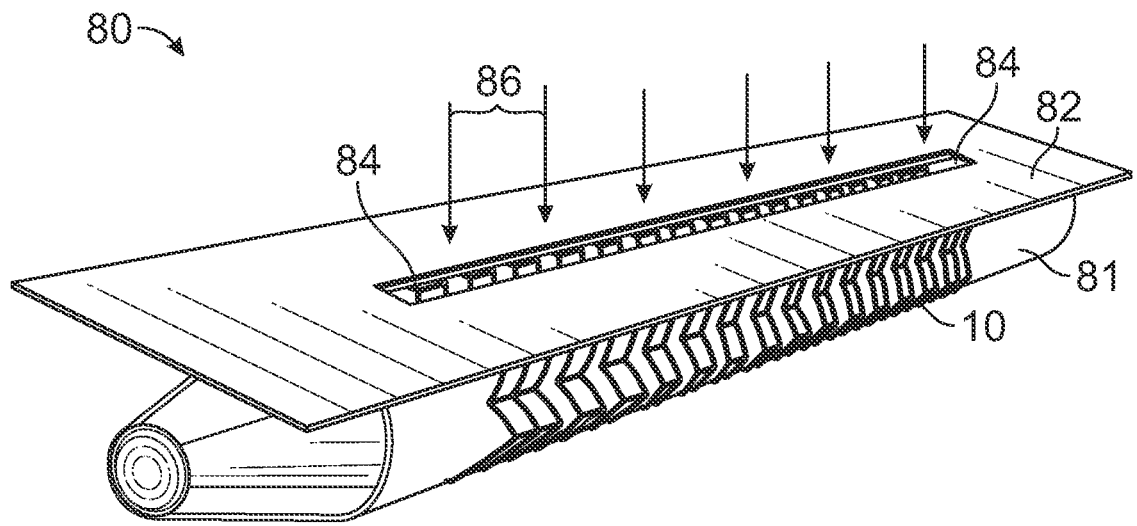
FIG. 16 is a perspective view of a system for forming a radiopaque layer on the inventive stent in accordance with a sixth embodiment of the method of the present invention.
Figure 17:
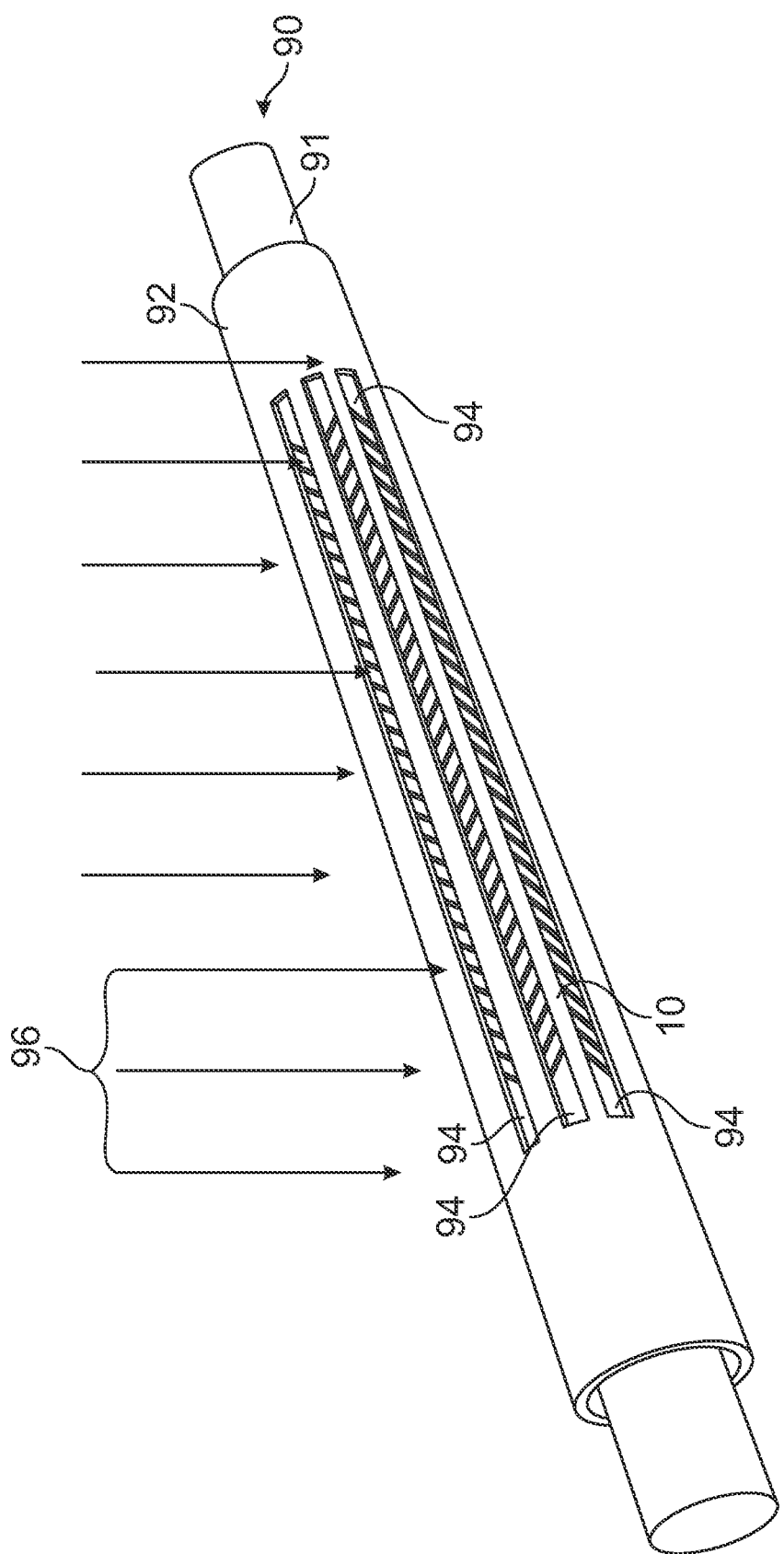
FIG. 17 is a perspective view of a system for forming a radiopaque layer on the inventive stent in accordance with a sixth embodiment of the method of the present invention.
Figure 18:
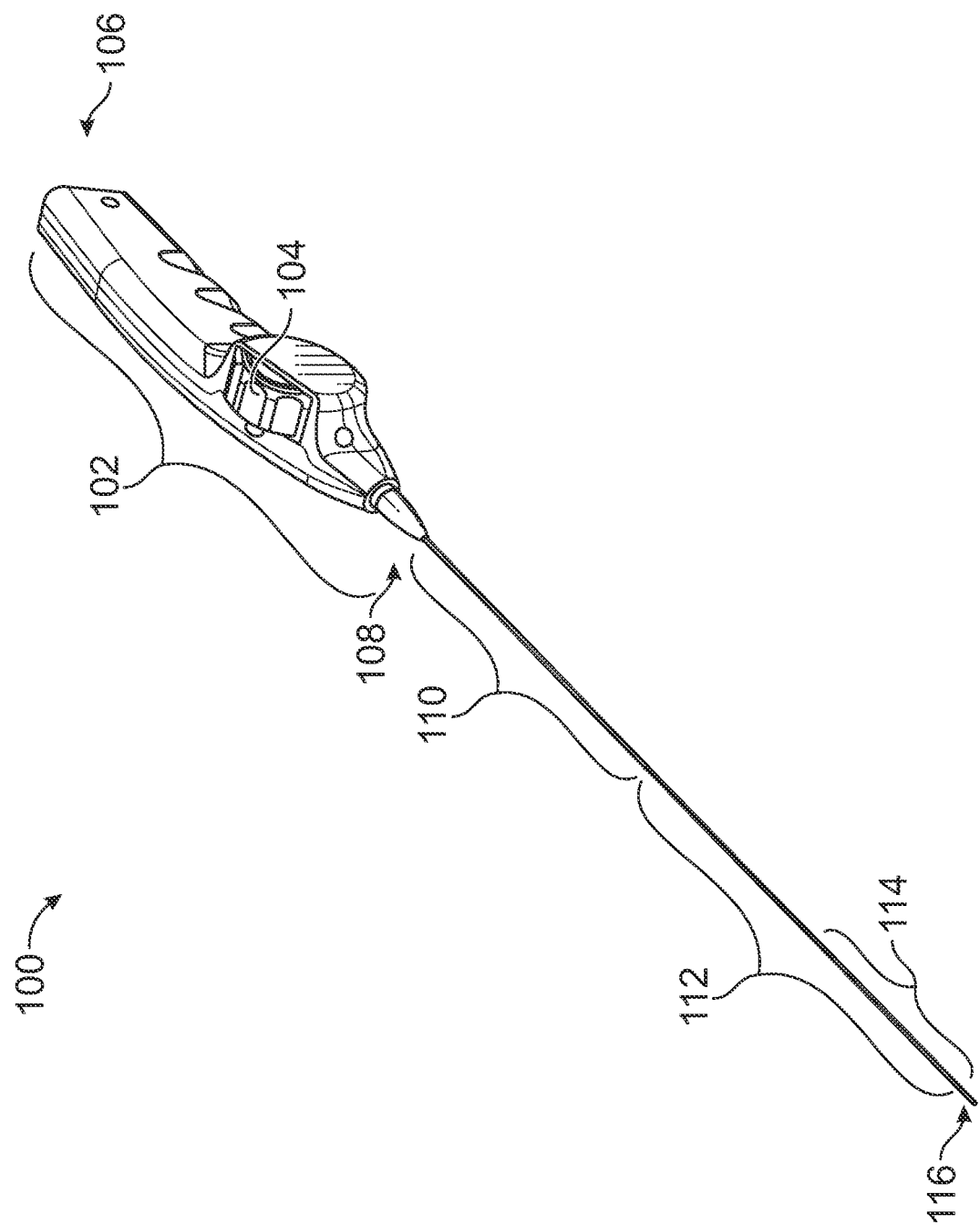
FIG. 18 is perspective view of a delivery system for the inventive embodiments of the inventive stent.
Figure 19:
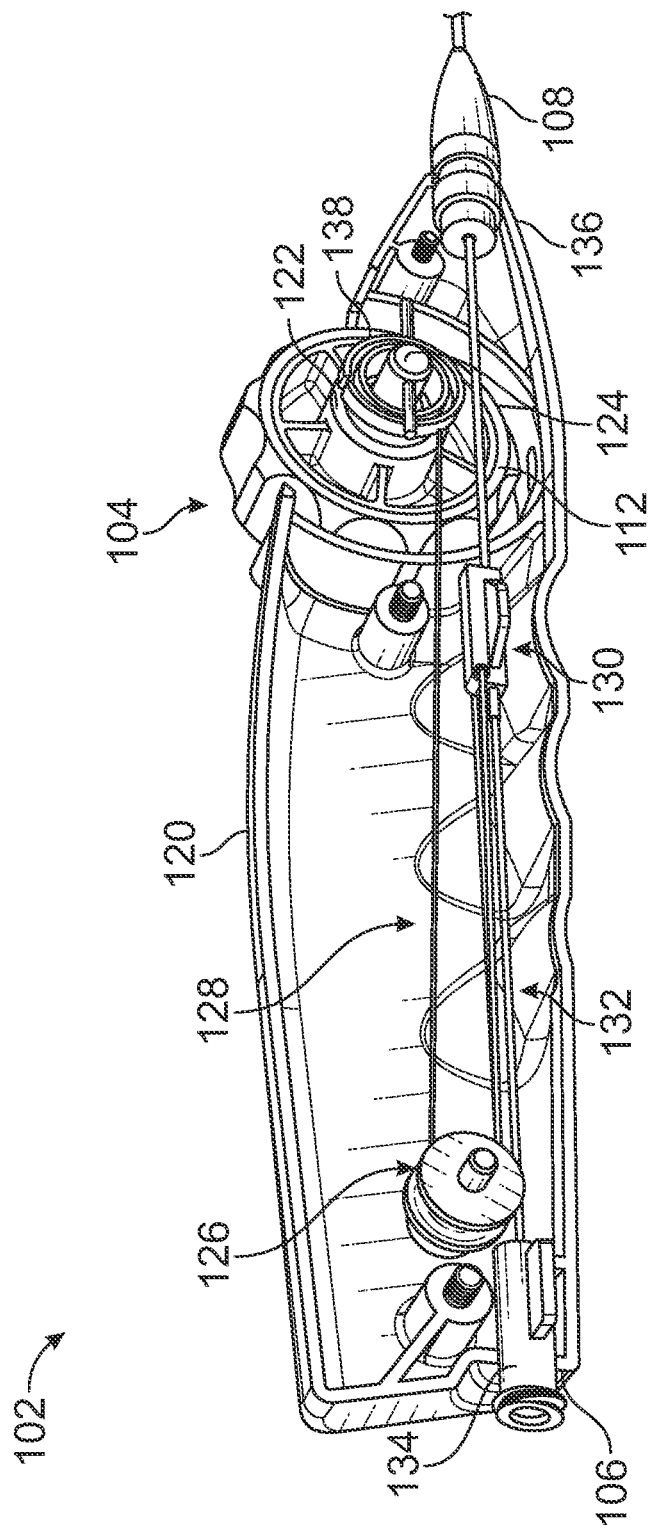
FIG. 19 is a fragmentary side elevational view of a delivery system handle in accordance with the present invention.

Turning now to methods of applying the radiopaque coating 72 to the stent 70, FIGS. 16 and 17 illustrate alternative systems and methods for applying the radiopaque coating 72. FIG. 16 illustrates the system and method 80 for applying the radiopaque coating 72 through a planar mask, whereas FIG. 17 illustrates the system and method 90 for applying the radiopaque coating 72 through a cylindrical mask.

The system and method 80 for applying the radiopaque coating 72 through a planar mask 82 is shown in FIG. 16. Stent 30, 70 is on a mandrel 81. The planar mask 82 has a planar mask window 84 that has a length that is greater than or equal to the length of the stent 30, 70 and a width that is less than or equal to the circumferential width of the radiopaque coating 72 to be applied to the low-stress or low-strain regions of the stent 30, 70. In accordance with the method 80 of the present invention, the radiopaque coating 72 is sputter coated 86 through the planar mask window 84 and onto the low-stress or low-strain regions of the stent 30, 70. The mandrel 81 is rotated about its longitudinal axis and metered so that only the low-stress or low-strain regions of the stent 30, 70 are exposed to the planar mask window 84 during each sputter deposition run. The mandrel 81 also protects the inner surface of the stent 30, 70 from the radiopaque coating 72 as it is in intimate contact with the inner surface of stent 30, 70. The planar mask 82 is maintained in sufficient proximity to stent 30, 70 during the sputter deposition run so that there is no or acceptable levels of overspray of the radiopaque coating 72 onto undesired stent regions.

The system and method 90 for applying the radiopaque coating 72 through a cylindrical mask 92 is shown in FIG. 17. Stent 30, 70 is on a mandrel 91 and in intimate contact with the mandrel such that the inner or luminal surface of the stent 30, 70 is shielded. The cylindrical mask 92 has a plurality of cylindrical mask windows 94, has a length that is greater than or equal to the length of the stent 30, 70 and a width that is less than or equal to the circumferential width of the radiopaque coating 72 to be applied to the low-stress or low-strain regions of the stent 30, 70. In accordance with the method 90 of the present invention, the radiopaque coating 72 is sputter coated 96 through at least one of the plurality of cylindrical mask windows 94 and onto the low-stress or low-strain regions of the stent 30, 70. The mandrel 81 and stent 30, 70 may be rotated, or the entire assembly of the mandrel 81, stent 30, 70 and cylindrical mask 92 may be rotated about the assembly's longitudinal axis, or the mandrel 81 and stent 30,70 may be maintained stationary and the cylindrical mask 92 rotated about its longitudinal axis and over the mandrel 81 and stent 30,70. In any case, the rotation is metered so that only the low-stress or low-strain regions of the stent 30, 70 are exposed to at least one cylindrical mask window 94 during each sputter deposition run. Multiple magnetrons having different angular orientations may be employed to accomplish depositing the radiopaque coating 72 without the need for rotation of the stent 30, 70 during the deposition run. The cylindrical mask 82 is maintained in sufficient proximity to stent 30, 70 during the sputter deposition run so that there is no or acceptable levels of overspray of the radiopaque coating 72 onto undesired stent regions. In addition or alternatively, an overspray mask (not shown) may be employed such that unacceptable levels of overspray during sputter coating 96 of the radiopaque coating 72 are avoided.

As an alternative to sputter depositing the radiopaque coating, the radiopaque coating may be applied by selective plating or other methods, including, for example, electroplating, brush plating, electroless chemical plating, or 3D printing.

In accordance with either system and method 80 or system and method 90 for depositing the radiopaque coating 72 onto stent 30, 70, the radiopaque coating 72 will have a thickness dependent upon the radiopaque material employed, as different radiopaque materials have differing degrees of opacity under fluoroscopy. Typically, however, the radiopaque coating 72 will have a thickness between about 2 μm and 10 μm.

Where the stent 30, 60, 70 has grooves 62, the grooves 62 may be formed in the outer surface 34 of the stent 30, 60, 70 and then the radiopaque coating 72 is sputter coated onto the outer surface 34 and into the grooves 62. Alternatively, the radiopaque coating 72 may be sputter coated onto the outer surface 34 before the grooves 62 are formed into the outer surface 34. In this latter case, the grooves 62 will be formed in the radiopaque coating 72 and, depending upon the thickness of the radiopaque coating 72 and the depth of the grooves 62, the grooves 62 may pass through the radiopaque coating and into the outer surface 34 of the stent 30, 60, 70.

Additionally, in accordance to the embodiment of the invention where a drug coating 68 is employed, the drug-coating 68 will be an outermost layer covering the radiopaque coating 72 and the grooves 62, if present.

As with all stents, the peripheral stents 10, 30, 60, 70 of the present invention require a delivery system to introduce and delivery the stent to a desired in vivo position. FIGS. 18-20B illustrate an embodiment of a delivery system 100 in accordance with the present invention. As is common to stent delivery systems, a retractable sheath 110 covers a catheter 112. Catheter 112 will typically have a guidewire lumen that passes either through its entire length in an over-the-wire version or passes along a more distal portion of the catheter 112 length in a rapid-exchange version. A stent mounting region 114 is at a distal end of the catheter 112 and the catheter 114 terminates at its distal end with an atraumatic tip 116. Retractable sheath 110 is capable of reciprocal coaxial movement along a portion of the length of the catheter 112. Sheath 110 will extend to the distal end of the catheter 110 and constrain the stent carried on the catheter 112 and typically abuts the atraumatic tip 116 in its extended state for delivery. Once positioned at a desired situs in vivo the sheath 110 is retracted proximally to expose and deploy the stent.

Handling of the catheter 112 and sheath 110 typically involves manipulating some sort of mechanism operably coupled to the catheter 112 and sheath 110 and capable of being controlled by an operator. In accordance with the delivery system 100 of the present invention, handle 102 is provided with a control actuator 104 and a flush port 106 to allow for flushing fluid to be applied through a lumen, such as the guidewire lumen, in the catheter 110.

Handle 102 consists mainly of a housing 120 which contains the control actuator 104 and into which the catheter 112 or a support tube 132 coupled to a proximal end of catheter 112 on its distal end and to a flush luer 143 coupled to the flush port 106 in the housing 120. The sheath 110 and the catheter 112 or support tube 132 pass through a strain relief member 108 and, optionally, a retaining member 136, both of which allow the sheath 112 to pass through and into the housing 120. A carrier member 130 is coupled to a proximal end of the sheath 112. The carrier member 130 is, in turn, operably coupled to the control actuator 104 such that the control actuator 104 applies a motivating force to the carrier to retract or extend the sheath 112.

Figure 20A:
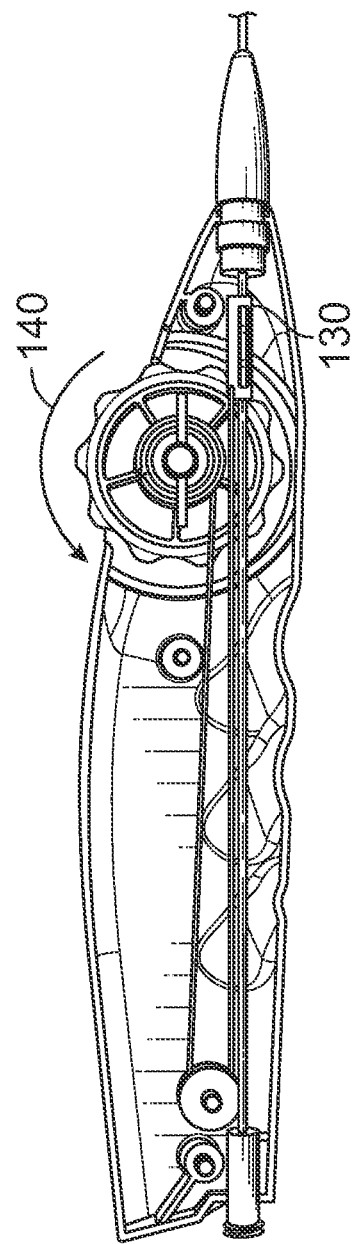
FIG. 20A is a fragmentary side elevational view of the delivery system handle in accordance with the present invention illustrating the handle where the stent is in an un-deployed state.
Figure 20B:
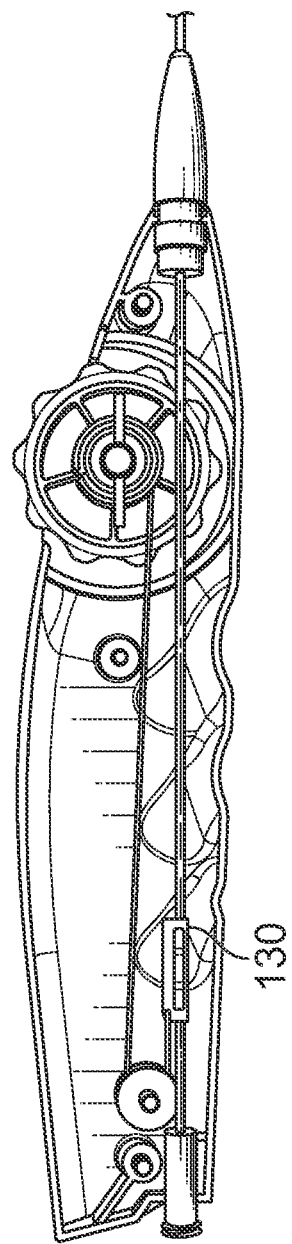
FIG. 20B is a fragmentary side elevational view of the delivery system handle in accordance with the present invention illustrating the handle where the stent is in a deployed state.
Figure 21:
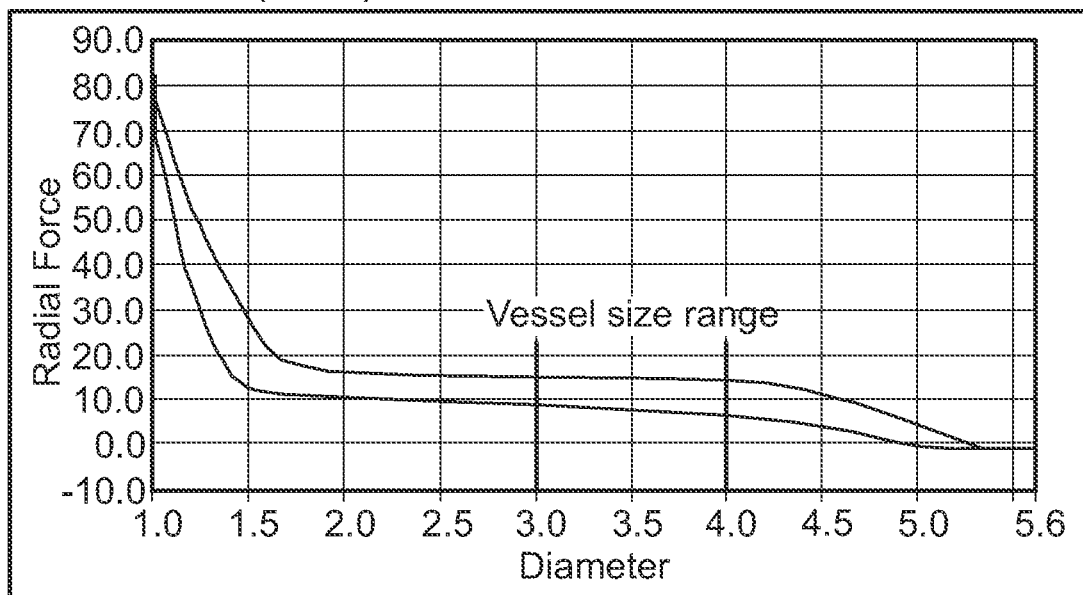
FIG. 21 is a radial force curve vs. expansion diameter for an exemplary 5.2 mm×30 mm stent in accordance with the present invention.
Figure 22:
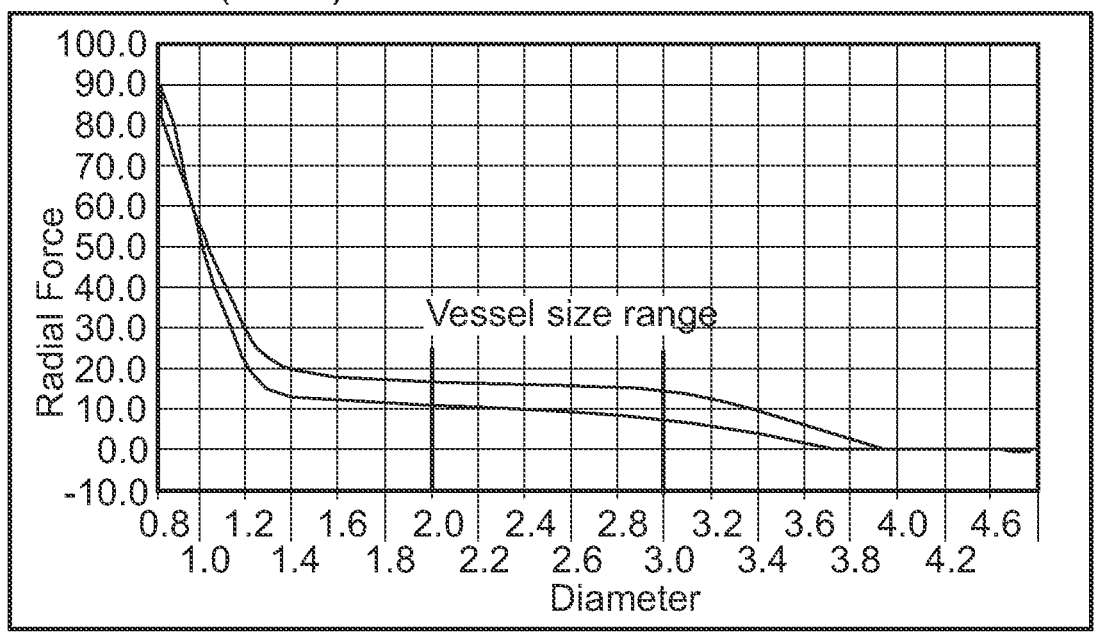
FIG. 22 is a radial force curve vs. expansion diameter for an exemplary 3.8 mm×30 mm stent in accordance with the present invention.

In accordance with an embodiment of the delivery system 100 of the present invention, the control actuator 104 is a rotary wheel having a unidirectional mechanism 122, such as a one-way bearing or ratchet, mounted on an axle 124 and coupled to the rotary wheel. A hub 138 is coaxially mounted on the axle 124 and operably coupled to the rotary wheel and/or the one-way bearing 122. An idler pulley 126 is mounted within the housing 120 in spaced apart relationship to the control actuator 104 and a drive member 128, such as a string, belt or wire, is coupled at one end to the hub 138 and on its opposing end to the carrier 130. The drive member 128 is passes over the idler pulley 126 and wraps around and unwraps from the hub 138 by actuation of the control actuator as the carrier reciprocally tracks on the catheter 112 or the support tube 132. In this manner, the catheter 112 is retained in a fixed position relative to the handle 102 and the sheath 110 is retracted or extended over the catheter 112 under the influence of the control actuator 104. FIG. 20A illustrates the extended position of the sheath 110 with the carrier 130 in proximal position, whereas FIG. 20B illustrates the retracted position of the sheath with the carrier 13 in a distal position.

The invention claimed is:

1. A method of making a stent, comprising the steps of:
   a. Providing a stent hypotube;
   a. Patterning a stent pattern in the stent hypotube to define the stent, the stent comprising a plurality of circumferential ring members having peaks and valleys, wherein the plurality of circumferential ring members is configured to nest with adjacent circumferential ring members when the stent is in a diametrically unexpanded state and a plurality of bridge members interconnecting adjacent pairs of circumferential ring members;
   b. Forming a plurality of volume-enhancing features in or on an outer abluminal surface of the defined stent wherein the volume-enhancing features are configured to add between about 20% to about 80% more surface volume to the outer abluminal surface of the stent as compared to a stent surface without the plurality of volume-enhancing features;
   c. Releasing the defined stent from the stent hypotube; and
   d. Coating the outer abluminal surface of the defined stent with a drug-eluting coating and at least substantially filling the plurality of volume-enhancing features.

2. The method of claim 1, wherein the step of providing a stent hypotube further comprises the step of making the stent hypotube from a binary, ternary or quaternary shape memory or superelastic material.

3. The method of claim 2, wherein the step of providing a stent hypotube further comprises the step of alloying a radiopaque material with shape memory or superelastic material.

4. The method of claim 1, further comprising the step of coating at least a portion of the released stent pattern with a radiopaque material prior to conducting the step [e] of coating the outer abluminal surface of the defined stent with a drug-eluting coating.

5. The method of claim 1, further comprising the step of coating low-stress regions of the released stent with a radiopaque material.

6. The method of claim 1, wherein the step of patterning the stent pattern in the stent hypotube further comprises the step of:
   c. Forming a plurality of projection members extending from at least one of a proximal and a distal circumferential ring member at proximal and/or distal ends of the stent pattern.

7. The method of claim 6, wherein the drug eluting layer substantially fills the plurality of volume-enhancing features and has a thickness of between about 3 µm to about 20 µm from the outer abluminal surface of the stent.

8. The method of claim 6, wherein the plurality of volume-enhancing features are formed in the plurality of circumferential ring members and in the plurality of bridge members.

9. The method of claim 6, wherein each of the plurality of projection members further comprises a substantially quadrilateral frame having a central open region.

10. The method of claim 9, further comprising a radiopaque cuff member joined to the plurality of projection members.

11. The method of claim 10, wherein the radiopaque cuff member has a portion thereof recessed within the central open region.

12. The method of claim 1, further comprising a radiopaque coating on at least a portion of the outer abluminal surface of the stent.

13. The method of claim 6, wherein the plurality of circumferential ring members and the plurality of bridge members further define a plurality of open cells.

14. The method of claim 13, wherein the plurality of open cells further comprises at least two different open cell configurations.

15. The method of claim 14, where the at least two different open cell configurations further comprise a first open cell configuration positioned at or proximate to opposing ends of the stent and a second open cell configuration positioned along an intermediate portion of the stent.

16. The method of claim 15, wherein the first open cell configuration further comprises a generally V-shaped open cell configuration.

17. The method of claim 15, wherein the second open cell configuration further comprises a generally Z-shaped open cell configuration.

18. The method of claim 1, wherein the plurality of volume-enhancing features further comprise a plurality of elongate grooves.

19. The method of claim 18, wherein the plurality of elongate grooves are oriented substantially parallel to a longitudinal axis of the stent.

20. The method of claim 1, wherein the plurality of circumferential ring members further has a substantially zig-zag configuration.

21. The method of claim 20, further comprising an offset section intermediate circumferentially adjacent peaks and valleys of each circumferential ring member.

22. The method of claim 1, wherein the plurality of circumferential ring members and the plurality of bridge members have a wall thickness between about 50 µm and about 100 µm.

23. The method of claim 1, wherein the plurality of volume-enhancing features have a depth between about 0.5 µm and about 10 µm.

24. The method of claim 23, wherein the plurality of volume-enhancing features have a spacing of about 2 µm and about 10 µm between adjacent volume-enhancing features.

25. The method of claim 1, wherein each of the plurality of volume-enhancing features have a width between 0.5 µm and 10 µm.

26. The method of claim 1, wherein each of the plurality of volume-enhancing features have a width to depth ration between about 1:1 and 1:3.

* * * * *